US009371960B2

(12) United States Patent
Lorimer et al.

(10) Patent No.: US 9,371,960 B2
(45) Date of Patent: Jun. 21, 2016

(54) APPARATUS FOR USE ON A CABLE; AND A SYSTEM FOR AND METHOD OF INSPECTING A CABLE

(71) Applicants: UNIVERSITY OF KWAZULU-NATAL, Durban (ZA); ESKOM HOLDINGS SOC LIMITED, Johannesburg (ZA)

(72) Inventors: Trevor Gareth Lorimer, Durban (ZA); Edward Sidney Boje, Cape Town (ZA)

(73) Assignees: UNIVERSITY OF KWAZULU-NATAL, Kwazulu-Natal (ZA); ESKOM HOLDINGS SOC LIMITED, Sandton (ZA)

( * ) Notice: Subject to any disclaimer, the term of this patent is extended or adjusted under 35 U.S.C. 154(b) by 0 days.

(21) Appl. No.: 14/417,734

(22) PCT Filed: Jul. 29, 2013

(86) PCT No.: PCT/IB2013/056208
§ 371 (c)(1),
(2) Date: Jan. 27, 2015

(87) PCT Pub. No.: WO2014/016814
PCT Pub. Date: Jan. 30, 2014

(65) Prior Publication Data
US 2015/0204480 A1 Jul. 23, 2015

(30) Foreign Application Priority Data
Jul. 27, 2012 (ZA) ..................................... 12/5693

(51) Int. Cl.
*G06F 19/00* (2011.01)
*F16M 13/02* (2006.01)
(Continued)

(52) U.S. Cl.
CPC ............. *F16M 13/02* (2013.01); *G01N 21/952* (2013.01); *H02G 1/02* (2013.01); *Y10S 901/02* (2013.01)

(58) Field of Classification Search
CPC combination set(s) only.
See application file for complete search history.

(56) References Cited

U.S. PATENT DOCUMENTS 4,563,955 A * 1/1986 Tarassoff .............. B61B 12/127
104/168
5,103,739 A * 4/1992 Sawada .................... H02G 1/02
104/112
(Continued)

FOREIGN PATENT DOCUMENTS

WO 2007/036776 A1 4/2007

OTHER PUBLICATIONS

International Search Report, mailed Mar. 6, 2014, for PCT/IB2013/056208, 3 pages.

*Primary Examiner* — Jonathan L Sample
(74) *Attorney, Agent, or Firm* — Seed IP Law Group PLLC

(57) ABSTRACT

The invention relates to an apparatus for use on a cable, particularly to a power line or cable inspection and/or monitoring apparatus or robot. The apparatus typically comprises a power module to power the apparatus, a pair of links serially coupled via at least one joint, a gripper arrangement coupled to each link for attaching the apparatus to the cable, wherein each gripper arrangement is controllable to grip and/or release the cable as an end effector, and grip the cable as a base in a serial manipulator fashion; and a control arrangement configured at least to control displacement of the links and the gripper arrangements to grip and/or release the cable. The invention also extends to a method of inspecting and/or monitoring a cable; an inspection and/or monitoring system for inspecting a cable; and to a method of operating an apparatus on an elongate cable to avoid an obstacle.

20 Claims, 17 Drawing Sheets

(51) Int. Cl.
*G01N 21/952* (2006.01)
*H02G 1/02* (2006.01)

(56) References Cited

U.S. PATENT DOCUMENTS

| | | | | |
|---|---|---|---|---|
| 5,203,646 A | * | 4/1993 | Landsberger | B08B 9/049 104/138.2 |
| 5,226,368 A | * | 7/1993 | Brochand | B61B 12/06 104/173.2 |
| 5,550,476 A | * | 8/1996 | Lau | G01R 31/024 324/509 |
| 5,565,783 A | * | 10/1996 | Lau | G01R 15/142 324/127 |
| 6,583,869 B1 | * | 6/2003 | Sheridan | G01S 17/87 356/153 |
| 6,826,452 B1 | * | 11/2004 | Holland | B66C 1/663 318/566 |
| 7,430,932 B2 | * | 10/2008 | Mekhanoshin | G01R 15/142 340/12.32 |
| 2005/0017751 A1 | * | 1/2005 | Gunn | G01R 15/142 324/764.01 |
| 2008/0246507 A1 | * | 10/2008 | Gunn | G01R 1/22 324/764.01 |
| 2008/0301891 A1 | * | 12/2008 | Park | B08B 1/04 15/88.4 |
| 2013/0256613 A1 | * | 10/2013 | Hyde | H02G 1/02 254/134.3 R |

* cited by examiner

APPARATUS FOR USE ON A CABLE; AND A SYSTEM FOR AND METHOD OF INSPECTING A CABLE

BACKGROUND OF THE INVENTION

This invention relates generally to methods and apparatuses for inspecting and monitoring cables particularly overhead power cables or power lines. The invention relates more specifically to an apparatus for use on a cable, particularly to a power line or cable inspection and/or monitoring apparatus or robot; a method of inspecting and/or monitoring a cable; an inspection and/or monitoring system for inspecting a cable; and to a method of operating an apparatus on an elongate cable to avoid an obstacle.

In South Africa, and around the world, electricity utilities are required to inspect energised electrical power conductors power lines or cables as well as insulators, towers and associated hardware, and their immediate environment (including the right of way) to ensure safe and reliable operation of an electrical network.

Inspections are often done manually by a human operator which is often dangerous, labour intensive and leaves room for human error. In some instances inspection of power lines is performed aerially from a helicopter. However, aerial inspection comes at a great financial cost and also has human error associated therewith. In addition, aerial inspection via a manned helicopter poses danger to the helicopter crew, particularly in inclement weather, as they fly fairly close to the power lines.

Various autonomous or remote controlled line-mounted power line inspection apparatuses or machines have been provided which ameriolate the problems above. However, these apparatuses or machines have limited manoeuvrability and hence also limited monitoring or inspection capability. In this regard, t is desired to provide a different power line inspection apparatus which seeks to address and at least mitigate problems of many conventional inspection means and methodologies.

SUMMARY OF THE INVENTION

According to a first aspect of the invention there is provided an apparatus for use on a cable, the apparatus comprising:
 a power module adapted to power the apparatus;
 at least one pair of arms or links serially coupled via at least one joint such that the links are displaceable relative to each other;
 a gripper arrangement coupled to each link, the gripper arrangements being adapted for attaching the apparatus to the cable, wherein each gripper arrangement is controllable to grip and/or release the cable; and
 a control arrangement comprising one or more processors configured at least to control displacement of the links and the gripper arrangements to grip and/or release the cable, in use.

The gripper arrangement may be controllable to grip or release the cable as an end effector, or grip the cable as a base, in use. It will be appreciated that the gripper arrangement may be selectively controllable in an alternate fashion to operate as a base or end effector. This may be done, for example, move past an obstacle on the cable as will be described below.

The gripper arrangement may comprise at least two spaced apart gripper fingers, the gripper arrangement being controllable to displace one or both of the gripper fingers relative to the cable thereby to engage the cable.

The gripper arrangement may be controllable to grip the cable in first and second engagement positions, and release the cable in a disengaged position, wherein in the first engagement position, both gripper fingers engage the cable, substantially on opposite sides of the cable; wherein in the second engagement position, only one gripper finger engages the cable; and wherein in the disengaged position, both gripper fingers disengage from the cable.

In one example embodiment, the gripper arrangement may comprise a gripper frame connected in a serial fashion to the link via a gripper joint, wherein the two gripper fingers are provided on the gripper frame and are spaced apart by a cable locating zone such that, in use, actuation of the gripper joint while the cable is located in the cable locating zone causes the gripper fingers to grip or release the cable.

The gripper joint is either a revolute joint such that the gripper frame is substantially rotatable relative to the link on actuation of the revolute joint to grip or release the cable; or a prismatic joint such that the gripper frame, or part thereof, is substantially linearly displaceable relative to the link on actuation of the prismatic joint to grip or release the cable.

The at least one joint coupling the links may be a revolute core joint operable to displace at least one link substantially about a first axis, or a revolute link joint operable to displace at least one link substantially about a second axis transverse to the first axis, in use.

It will be understood that, in use, the apparatus may be a serial manipulator, or may operate in a serial manipulator fashion, in that one gripper arrangement gripping the cable in the first engagement position serves as a base, and the other gripper arrangement in the disengaged position serves as an end effector.

One or both the gripper fingers may be gripper wheels or castors. Preferably, both gripper fingers are wheels.

The apparatus may comprise drive means drivingly coupled to one or both the wheels thereby to selectively cause rotation of one or both the wheels thereby to facilitate moving the apparatus longitudinally along the cable, in use.

Where both the gripper fingers are wheels, one wheel may have a larger diameter than the other wheel.

One or both wheels may comprise a circumferentially extending groove comprising traction means disposed therein to receive the cable therein, in use. The gripper fingers may be finger-like protrusions extending transversely from the gripper frame and may also comprise a similar groove comprising traction means.

In the first engagement position, further actuation of the gripper joint provides another degree of freedom to the apparatus as the apparatus is caused to displace relative to the line.

In a preferred example embodiment, each link may comprise an elongate first portion extending transversely from a second portion having a longitudinal axis, wherein second portions of the links are coupled via the at least one joint. The second portions of the links may be coupled to a revolute core joint, and wherein at least one second portion is coupled to the revolute core joint via a revolute link joint, wherein actuation of the revolute link joint causes rotational displacement of the link about the longitudinal axis of the second portion and actuation of the revolute core joint causes rotational displacement of one or both links about an axis perpendicular to the longitudinal axis of the second portion. Both second portions of the links may be coupled to the core joint via link joints.

The apparatus may comprise a payload body connected to one or more of a revolute core joint and a pair of revolute link joints.

The cable may be substantially of circular section and may be a current carrying conductor or power cable.

The apparatus may comprise one or more inspection, monitoring, and maintenance systems, wherein the apparatus is used for inspecting, monitoring, and performing maintenance on the cable.

The power module may comprise a transformer arrangement to draw power from the power cable.

The transformer arrangement may be operable to serve as a safety device to prevent the apparatus from falling from the power cable, in use.

The control arrangement may comprise a measurement determining module configured to determine one or more mechanical, thermal, acoustic, electrical, magnetic and electromagnetic properties associated with the power cable.

Each link may comprise or may be constructed from electrical components to enable the measurement determining module to determine electrical properties associated with power cable from measuring the properties associated with the links. In particular, each link comprises resistive portions or elements, thereby to facilitate the measurement determining module determining the voltage drop across the span of two links when both grip the power cable, thereby to facilitate determining at least electrical resistance of a splice. Instead, or in addition, the links may comprise electrical fuse portions or elements to serve as failsafe mechanisms should the apparatus fall out of an electrical clearance window of a power cable to which the same is attached.

In one example embodiment, the apparatus may comprise a resistive probe configured to facilitate charging of the apparatus to the potential of the power cable and to discharge the apparatus to the earth potential during placement and removal of the apparatus from the line.

The control arrangement may comprise a navigation module configured to receive command signals from a ground station, remote control means, or autonomous control signals generated autonomously onboard in order to control all or some of the links and the gripper arrangement.

The apparatus may comprise one or more image capturing means configured at least to capture images of the cable for inspection or navigation.

The image capturing means may comprise one or more from a group comprising visible light video cameras having wide field-of-view lenses, ultra violet and infra-red spectral cameras or imagers.

It follows that in some example embodiments, the navigation module may be configured at least to:
  receive the captured images from the one or both of the first and second image capturing means;
  process received captured images to determine a configuration of each link and/or gripper arrangement relative to the cable; and
  control the links and the gripper arrangements to grip, or release, the cable, in use.

Instead, or in addition, the navigation module may be configured to:
  receive data from one or more of a global positioning system, an inertial platform, and the inspection system;
  process received captured images to determine a configuration of each link and/or gripper arrangement relative to the cable; and
  control the links and the gripper arrangement to grip, or release, the cable, in use.

Though it may form part of the navigation module, the control arrangement may comprise an obstacle avoidance module configured to:
  receive captured images of the cable;
  process received captured images to determine whether an obstacle is in the path of the apparatus; and
  control each link and gripper arrangement to bypass the obstacle and to grip the cable at another zone thereof.

The obstacle avoidance module may be configured to:
  receive data from one or more of a global positioning system, an inertial platform, and the inspection system;
  process received captured images to determine a configuration of each link and/or gripper arrangement relative to the cable; and
  control the links and the gripper arrangement to grip, or release, the cable, in use.

The apparatus may comprise a communication means configured to receive and transmit data including commands for processing by the control arrangement.

The apparatus may comprise one or more actuators to control displacement of the gripper arrangements and/or links about the joints and/or to control actuation of the joints to cause displacement of the gripper arrangements and/or links.

According to a second aspect of the invention, there is provided a method of inspecting and/or monitoring a cable, the method comprising:
  providing on the cable an apparatus comprising a power module adapted to power the apparatus; at least one pair of links serially coupled via at least one joint such that the links are displaceable relative to each other; a gripper arrangement coupled to each link for attaching the apparatus to the cable, wherein each gripper arrangement is controllable to grip and/or release the cable; and a control arrangement comprising one or more processors configured to control displacement of the links and the gripper arrangements to grip and/or release the cable, in use;
  causing the apparatus to move on a cable by way of suitable control signals; and
  controlling one or both inspection and/or monitoring systems associated with the apparatus to collect data associated with the cable.

The method may comprise the step of operating the apparatus wirelessly under remote control. Instead, or in addition, the method may comprise operating the apparatus in an autonomous or semi-autonomous mode.

The method may comprise transmitting the collected data wirelessly from the device.

According to a third aspect of the invention, there is provided an inspection and/or monitoring system for inspecting a cable, the inspection system comprising:
  a database for storing data; and
  a receiver module configured to receive one or more signals comprising data associated with the cable from at least one apparatus comprising a power module adapted to power the apparatus; at least one pair of links serially coupled via at least one joint such that the links are displaceable relative to each other; a gripper arrangement coupled to each link for attaching the apparatus to the cable, wherein each gripper arrangement is controllable to grip and/or release the cable; and a control arrangement comprising one or more processors configured to control displacement of the links and the gripper arrangements to grip and/or release the cable, in use.

The system may comprise a control module operable to transmit one or more command signals to the apparatus to control one or more operations of the same.

It will be appreciated that the system may comprise one or more apparatuses as hereinbefore described.

The system may comprise a communication module configured to communicate wirelessly with each apparatus.

According to a fourth aspect of the invention, there is provided a method of operating an apparatus on an elongate cable to avoid an obstacle, wherein the apparatus comprises a power module adapted to power the apparatus; at least one pair of links serially coupled via at least one joint such that the links are displaceable relative to each other; a gripper arrangement coupled to each link for attaching the apparatus to the cable, wherein each gripper arrangement is controllable to grip and/or release the cable; and a control arrangement comprising one or more processors configured to control displacement of the links and the gripper arrangements to grip and/or release the cable, in use, the method comprising:

operating the gripping arrangement of one link of the apparatus to grip the cable such that the same serves as a base;

operating the gripping arrangement of the other link of the apparatus to release the cable thereby freeing up the same for spatial displacement as an end effector; and causing displacement of the links relative to each other and/or the base relative to the associated link thereby to move the end effector to a region on the cable, or jumper cable, beyond the obstacle; and causing the end effector to engage and grip the cable, or jumper cable, beyond the obstacle.

DESCRIPTION OF PREFERRED EMBODIMENTS

Figure 1:
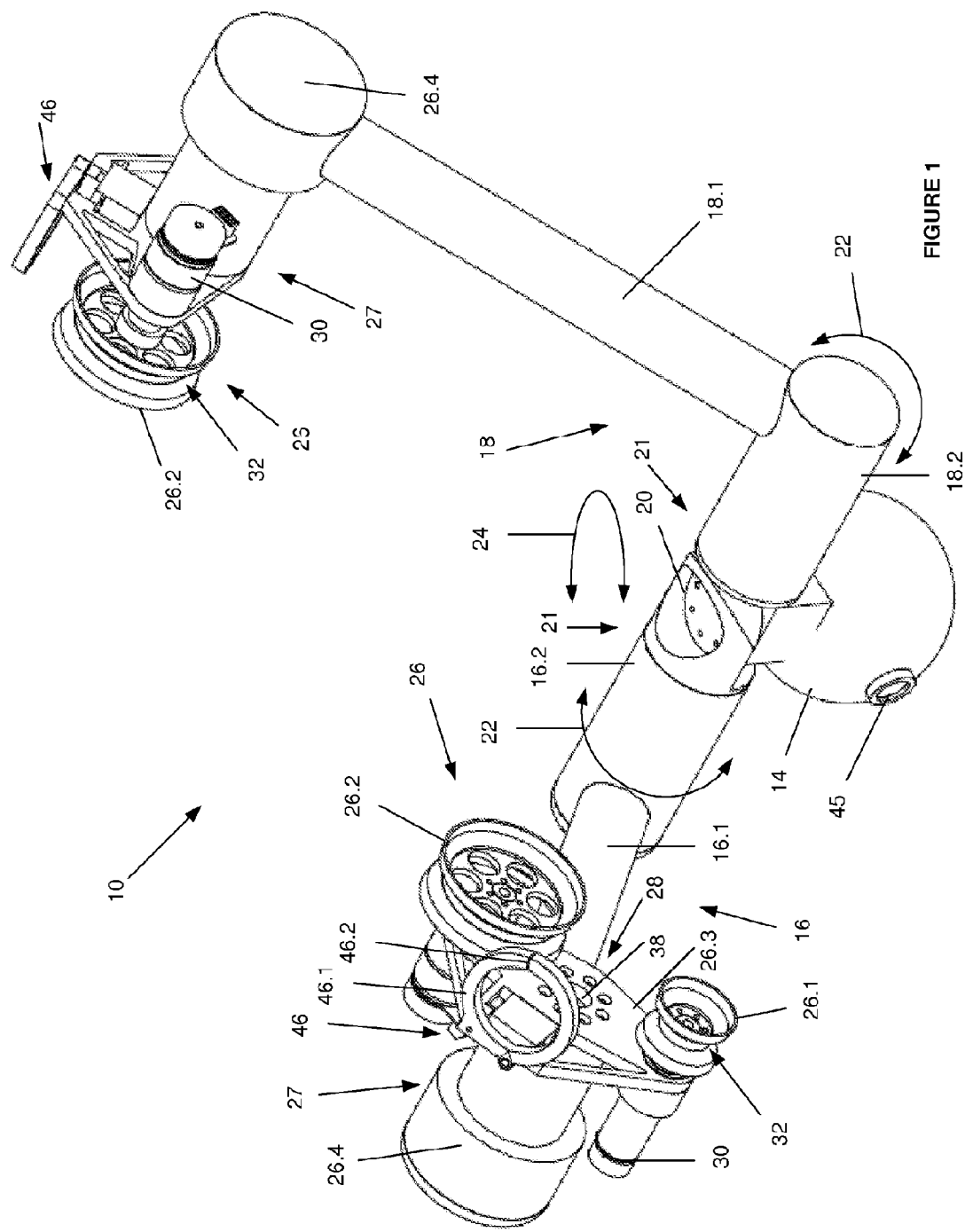
FIG. 1 shows a perspective view of an apparatus for use on a cable, particularly a power cable, in accordance with an example embodiment, with the body in a first position.

In the following description, for purposes of explanation, numerous specific details are set forth in order to provide a thorough understanding of an embodiment of the present disclosure. It will be evident, however, to one skilled in the art that the present disclosure may be practiced without these specific details.

Referring firstly to FIGS. 1 to 6 of the drawings, an apparatus in accordance with an example embodiment is generally indicated by reference numeral 10. The apparatus 10 is conveniently a power line apparatus or robot for use on a power line or cable 12 (FIGS. 5 and 7) of roughly circular cross section. However, it will be understood that the apparatus 10 may be used on any cable of substantially circular cross section, for example on communication lines or transport cables, for example, cable-car cables, or the like. The apparatus 10 is conveniently configured to move on a line 12, for example spanning between towers, as well as a jumper cable which is typically found on a strain tower for example where the line changes direction. The apparatus 10 may also move along an insulated rod or "hot stick", for example during deployment or recovery. However, for ease of explanation, reference will be made primarily to an example embodiment whereby the apparatus travels on the cable 12.

It will be understood that the terms "cable", "line", and "conductor" will be used interchangeably in the specification, unless in a different context, to describe the cable 12.

In any event, the apparatus 10 may effectively be a serial manipulator comprising a plurality of mechanical links connected in series by revolute and/or prismatic joints as will be discussed below. In the illustrated example embodiment, the apparatus 10 comprises a payload body 14 which is configured to be moved by the mechanical links. In some example embodiments, the components of the payload body 14 may be distributed throughout the body of the robot 10.

In one example embodiment, the payload body 14 is operatively connected to at least two mechanical arms or links 16 and 18 displaceable relative to the payload body 14. The payload body 14 may comprise any geometric shape. However, in the illustrated example, the body 14 comprises a sphere. The links 16, 18 may be substantially identical and therefore it will be appreciated that any description of one link 16, 18, and components associated therewith, may be extended to the other link 18, 16 respectively.

Figure 4:
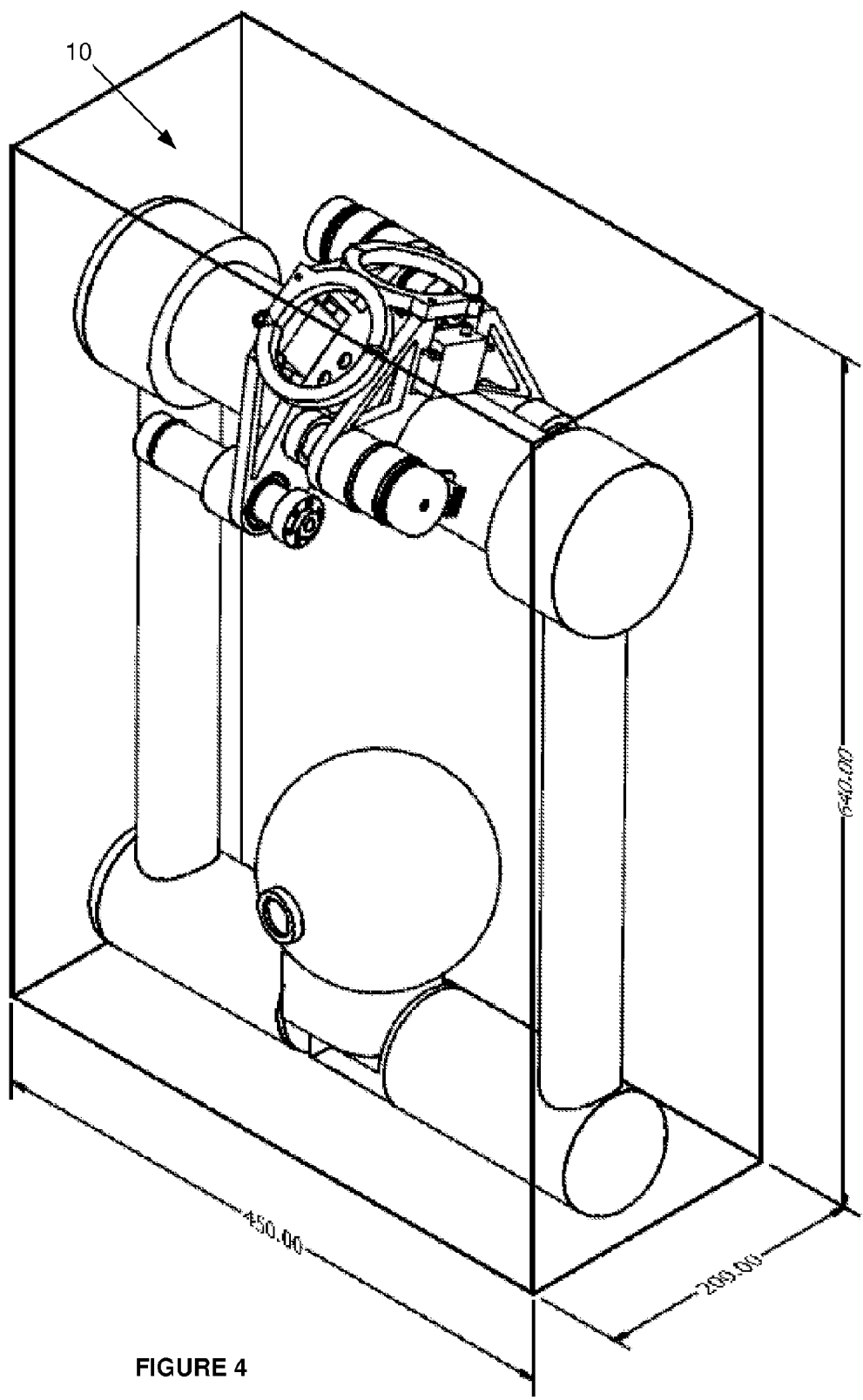
FIG. 4 shows a perspective view of the apparatus of FIG. 1 in a stowage condition in accordance with an example embodiment.

Though the links 16, 18 may be selected to be of different configurations, for example, parallel links or four-bar mechanisms, the links 16, 18 typically comprise elongate cylindrical links particularly first portions 16.1, 18.1 and shorter elbow second portions 16.2, 18.2. The second portions 16.2, 18.2 are connected to each other and to the payload body 14 via a revolute core joint 20. In an example embodiment, the second portions 16.2, 18.2 are connected to at least the core joint 20 via a pair of revolute link joints illustrated generally by reference numeral 21 (FIG. 1). The second portions 16.2, 18.2 are usually positioned parallel and collinearly or co-planar, spaced by the core joint 20 as illustrated. It will be appreciated that the second portions 16.2, 18.2 may extend transversely, particularly normal or perpendicular, to the first portions 16.1, 18.1 such that when the first portions 16.1, 18.1 are parallel, the links 16, 18 of the apparatus 10 provide substantially a U-shaped profile (e.g., as illustrated in FIG. 4). In addition, the second portions 16.2, 18.2 extend away from the body 14 and the core joint 20 such that the links 16, 18 are each disposed on opposite sides of the body 14.

To provide the required translational and rotational degrees of freedom to the apparatus 10, the second portions 16.2, 18.2, are rotatably displaceable relative to each other by way of the revolute core joint 20 as well as link joints 21. However, it will be understood that in some example embodiments, only one joint 21 is provided in the apparatus 10 as opposed to two as will be discussed below. For brevity, it will be understood that the core joint 20 and optionally in some example embodiments, link joints 21, may conveniently be controllable revolute joints comprising, or are operable, by suitable actuators such as motors (e.g., stepper, high torque servomotors, or the like) disposed in the housing/body of the apparatus 10 (not shown) to cause displacement of at least the links 16, 18. The joints are typically controllable in so far as the actuators controlling the same are controllable.

Instead, or in addition, each link may be actuable by the actuators such that they are displaceable about the joints.

It will be noted that the control of the joints 20 and 21 and/or links 16, 18 about the joints 20 and 21 may be achieved in a plurality of conventional ways, as is well understood in the field of invention, and therefore should not detract from the invention described herein.

In one example embodiment, the second portions 16.2, 18.2, and hence the links 16, 18, are rotatable, or at least part rotatable, in the direction of arrows 22 via the joints 21, whereas the links 16, 18 are rotatable, or part rotatable, in the direction of arrow 24 via the core joint 20. It will be understood that the axis of rotation about the core joint 20 is transverse to the axis of rotation of the second portions 16.2, 18.2 about the link joints 21. In preferred example embodiments, the axis of rotation about the core joint 20 is typically perpendicular to the axis of rotation of the second portions 16.2, 18.2 about the joints 21 to ensure independence.

Figure 3:
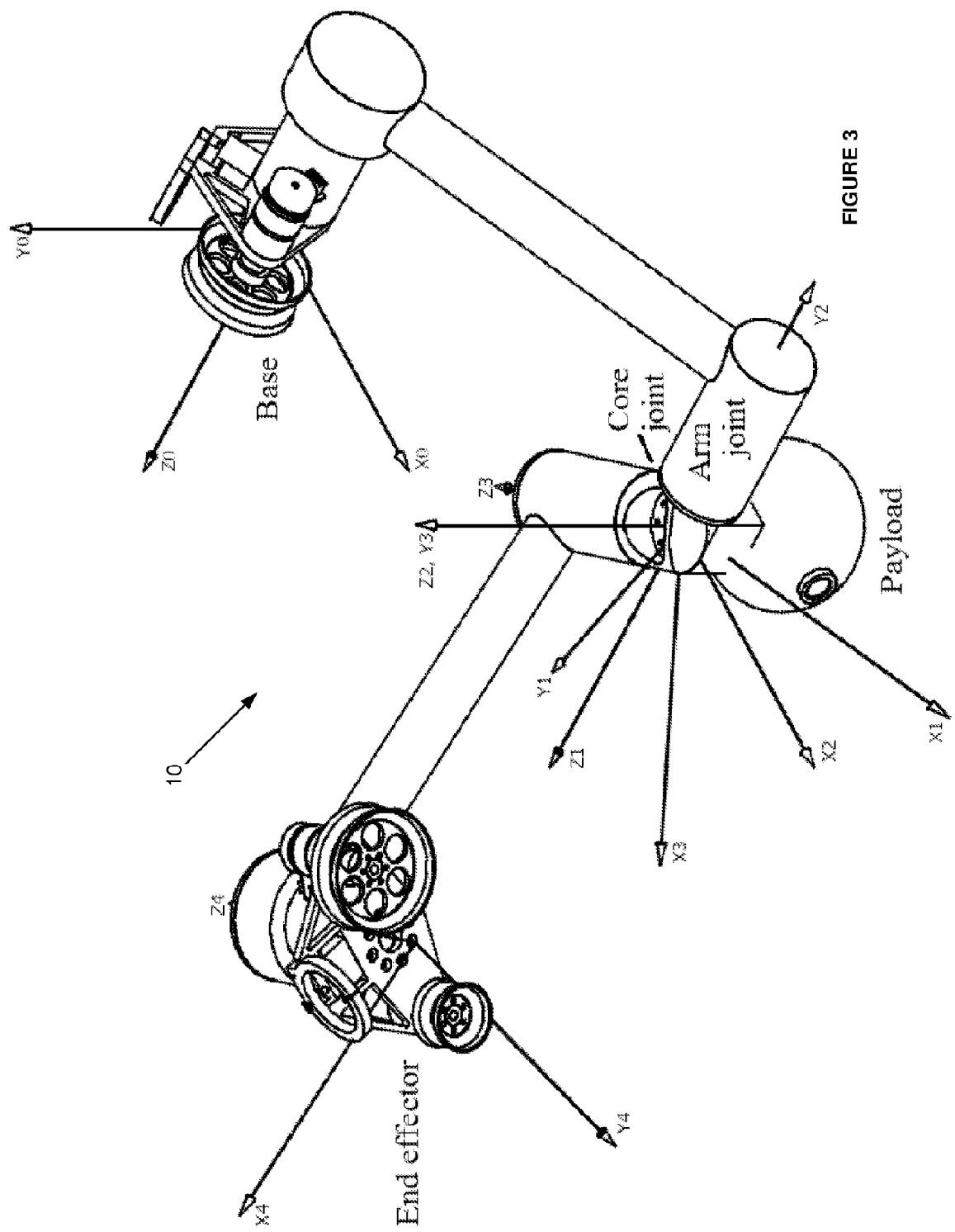
FIG. 3 shows a perspective view of the apparatus of FIG. 1 with one link displaced relative to the other link in accordance with an example embodiment.

The core joint 20 and the second portions 16.2, 18.2 are configured such that operation of the core joint 20 takes the second portions 16.2, 18.2 out of alignment (as can be seen in FIG. 3). This eliminates a singularity configuration (gimbal lock) which normally exists due to the collinear alignment of the link joints portions 16.2, 18.2, and allows for three degrees of freedom at end portions of the manipulator link 16, 18, as will be described below. It will be appreciated that the number of degrees of freedom matches the number of joints, provided there are no singularities in the configuration.

Figure 2:
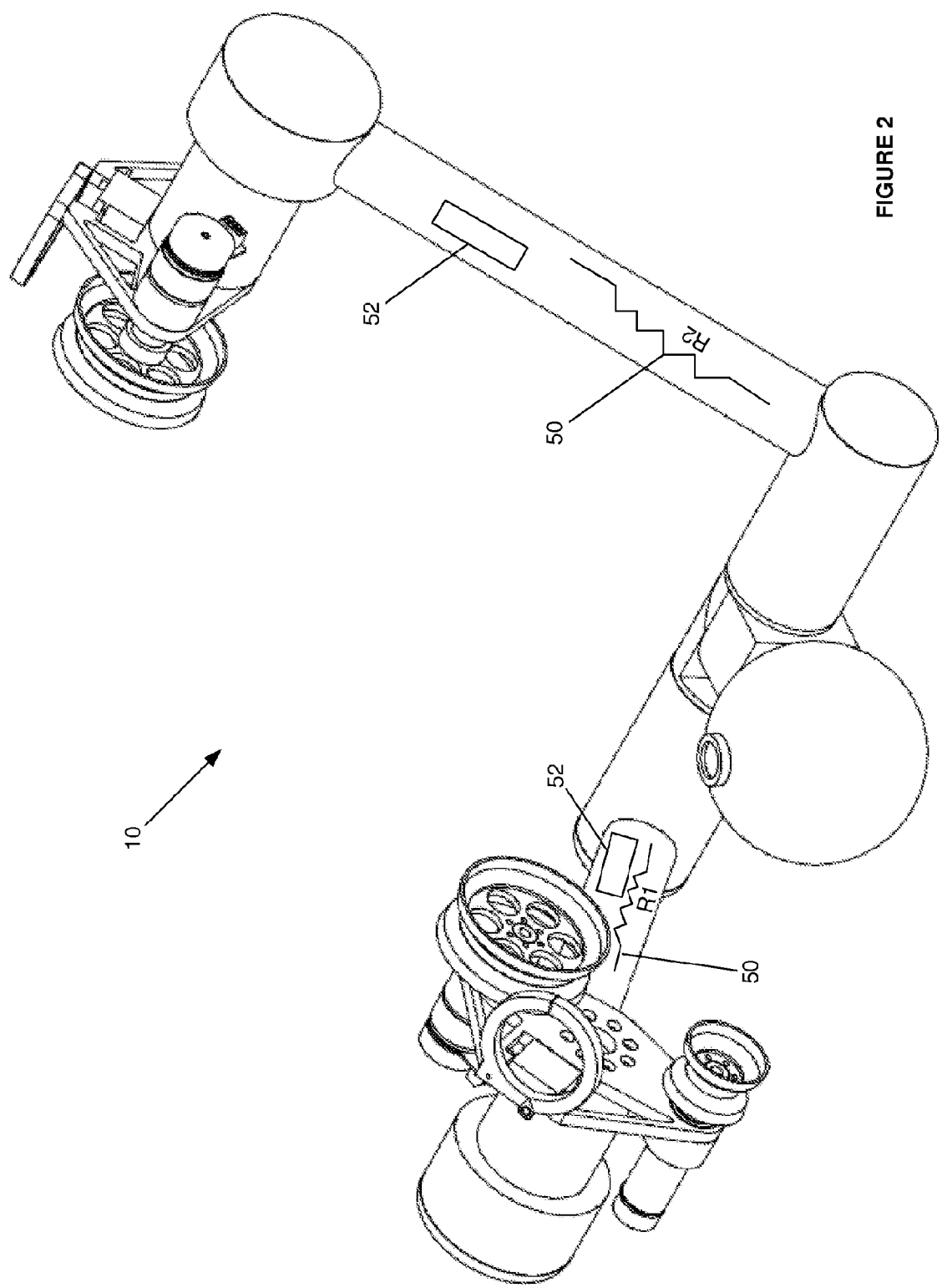
FIG. 2 shows a perspective view of the apparatus of FIG. 1, with the body in a second position in accordance with an example embodiment.

As alluded to above, the payload body 14 is connected to the core joint 20. In this regard, the singularity configuration that occurs when the second portions 16.2, 18.2 are collinear and parallel allows for the payload body 14 position to be changed (without affecting the manipulator link position), for example, as illustrated in FIGS. 1 and 2.

In a preferred example embodiment, the links 16, 18 comprise a gripper arrangement 26 at end portions of the first portions 16.1, 18.1 to alternately, or simultaneously as the case may be, grip or attach to, the line 12 and selectively release, or detach, from the line 12 such that when attached to the line 12, most of the apparatus 10 hangs below the line 12. In particular, when one gripper arrangement 26 of one link, e.g., link 16 is detached from the line 12 and the gripper arrangement 26 of the other link 18 is attached to the line, the apparatus 10 may typically be a serial manipulator essentially comprising several mechanical links connected in series by revolute and/or prismatic joints with the attached gripper arrangement 26 of the link 16 being a base and the link 18 (particularly the detached gripper arrangement 26 of the link 18) being an end effector. Similarly, when the link 18 is attached to the line 12 and the link 16 is detached from the line 12, the gripper arrangement 26 of the link 18, may be the base and the gripper arrangement 26 of the link 16 may be the end effector. In this way, the manoeuvrability of the apparatus 10 on the line 12 is increased as described below.

Each gripper arrangement 26, when operated to attach to the line 12, is configured to bear the weight of the apparatus 10 and provide sufficient torque to hold the apparatus 10 suspended beneath the line 12 while under the influence of gravity.

It will be noted that the apparatus 10 is configured to move its end effector (detached gripper arrangement 26) in three dimensions to reach around obstacles or in any other way locate the detached gripper arrangement 26 within its workspace, and at an angle to the vertical plane in-line with the line/main conductor 12. The end effector or gripper arrangement 26 has three translational degrees of freedom of movement. However, it will be appreciated that the gripper arrangement 26 also needs to be oriented correctly to attach to the line 12. In this regard, it will be understood that to fully control the orientation of the gripper arrangement 26 from the rest of the manipulator, three additional rotational degrees of freedom are required.

To reduce the complexity of a conventional six degree-of-freedom, the orientation degrees of freedom of the gripper arrangement 26 are limited. This may be achieved by exploiting the shape of the line 12. Due to the typical substantially circular cross section of the line 12, the gripper arrangement 26 may approach the jumper from any direction perpendicular to the line 12, therefore one less degree of freedom is required. Thus, in terms of negotiating obstacles, five degrees of freedom are sufficient for attaching to jumpers. If simply reaching around a suspension clamp, damper or similar obstacle, four degrees of freedom are sufficient since the target line is in-plane with the base line but in the case of a suspension clamp (or jumper), the target line is not collinear in the place, so the robot 10 requires at least one orientation degree of freedom.

To this end, the gripper arrangement 26, in a preferred example embodiment, comprises at least two gripper fingers in the form of wheels 26.1 and 26.2 controllable to be displaceable relative to the cable 12, in use, thereby to grip and release the cable 12. In particular, the wheels 26.1, 26.2 are conveniently attached to a gripper frame 26.3 which is connected to a revolute gripper joint generally indicated by reference numeral 27 controllable or actuable by a suitable actuator (similar to the actuators as described above) located in housing 26.4. The revolute joint 27 may be a conventional controllable joint comprising an actuator shaft coupling the frame 26.3 to the actuator, a hub connected to the shaft and support bearings (not visible in the drawings). It follows that the comments above pertaining to the joints 20, 21 apply substantially to the joint 27.

The gripper frame 26.3, and hence the wheels 26.1, 26.2, is rotatable or part-rotatable relative to the links 16, 18 on actuation or control of the revolute joint 27 to grip or release the cable 12. It will be appreciated that the gripper frame 26.3 has the two wheels 26.1, 26.2 attachable thereto at spaced apart locations separated by a cable locating zone 28.

In some example embodiments, the gripper arrangement 26 comprises a single wheel and a stopper if the apparatus 10 is not expected to move on the line when the second link is detached.

Figure 5:
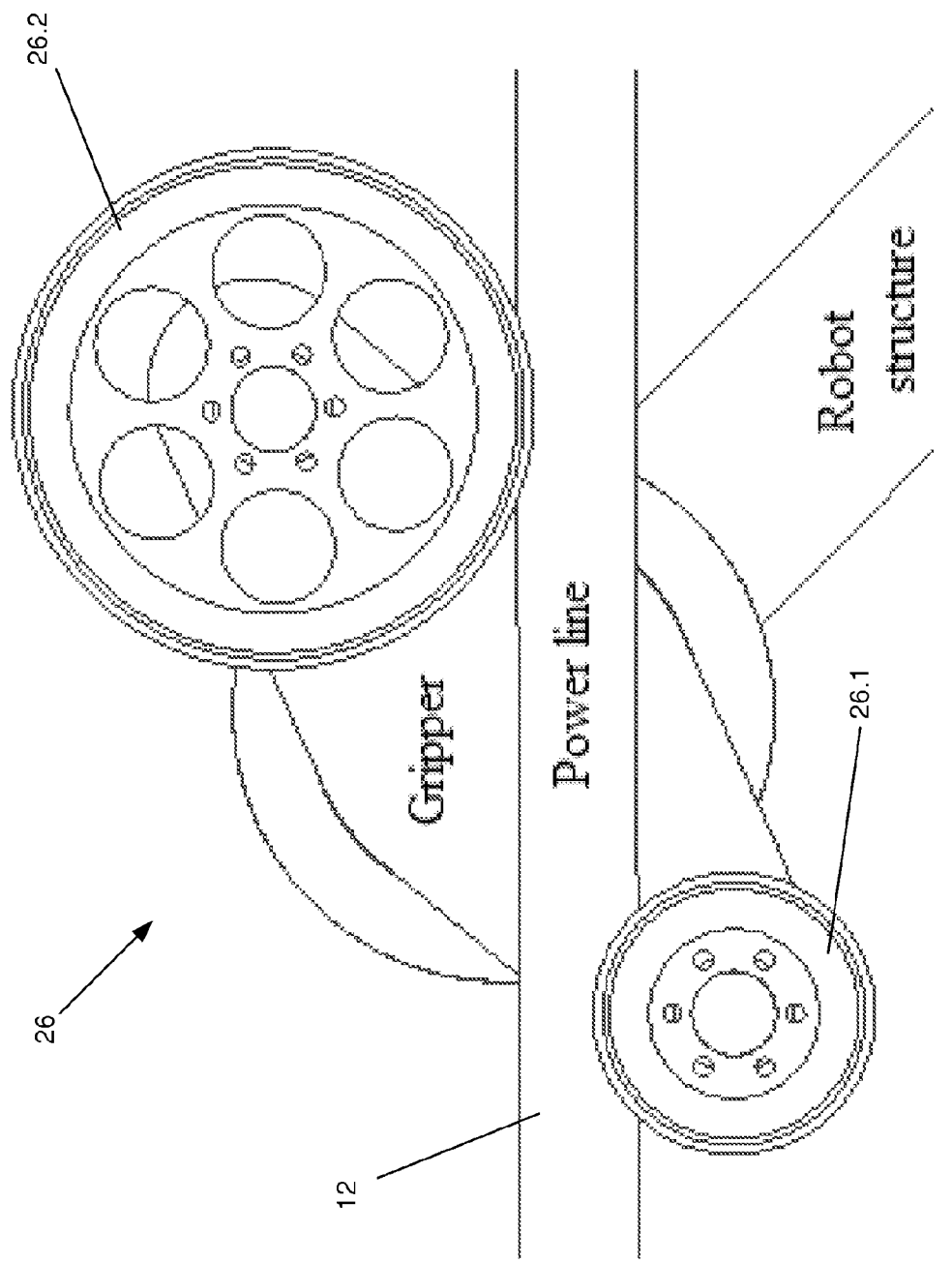
FIG. 5 shows a side view of part of the gripper arrangement of the apparatus of FIG. 1, in use, attached to the power cable in accordance with an example embodiment.
Figure 15:
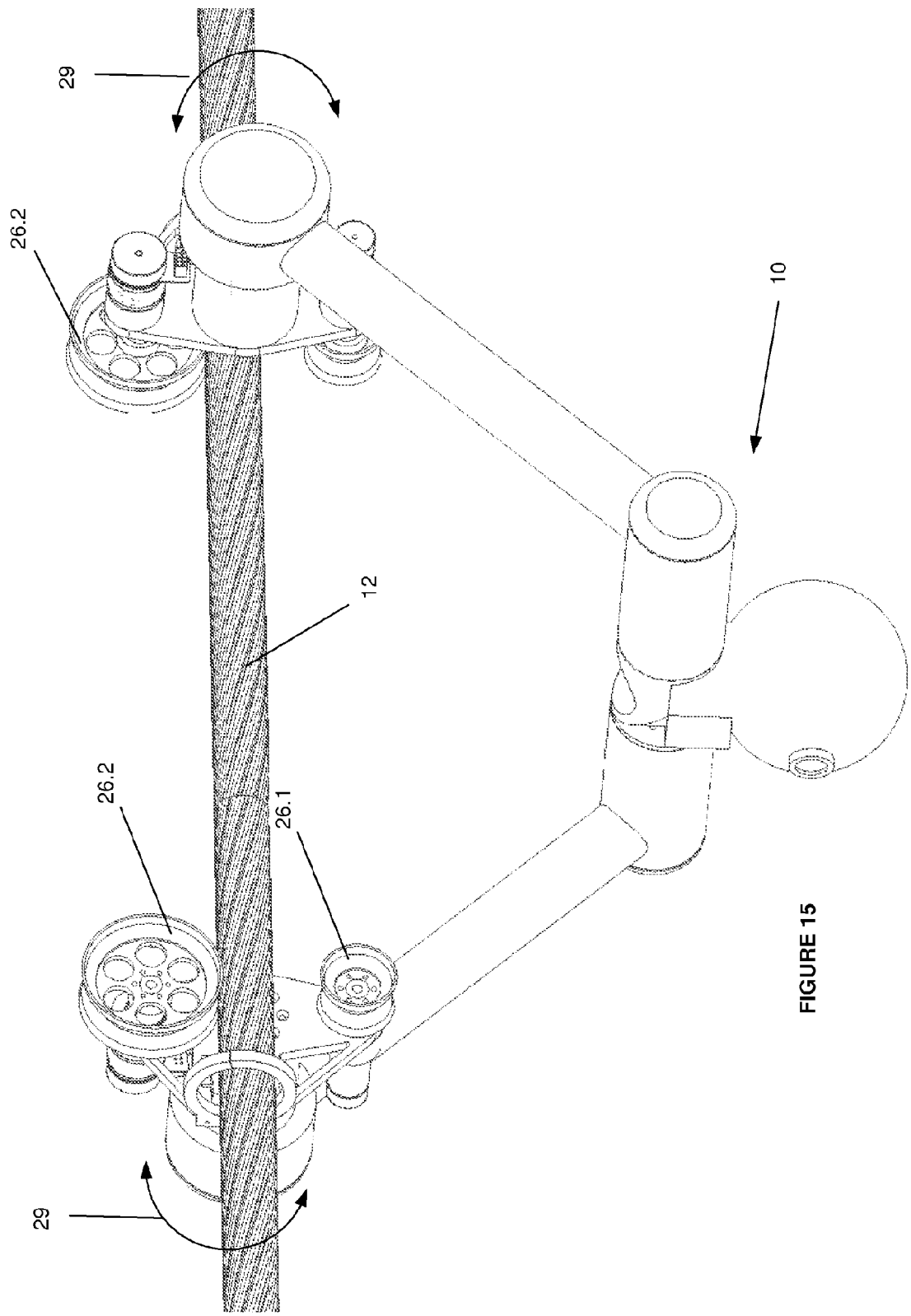
FIG. 15 shows a perspective view of the apparatus of FIG. 1 substantially, in use, on a line in accordance with an example embodiment illustrating the apparatus with the gripping arrangement in the second engagement position and the transformers acting as safety devices in the closed position around the line.

The wheels 26.1 and 26.2 may be rotatable to grip the cable 12 in a first engagement position and a second engagement position. In the first engagement position, both wheels 26.1, 26.2 grip the line 12 substantially at opposite sides of the line as illustrated in FIG. 5. In the second engagement position, only one wheel 26.2 of both links engages the cable 12, substantially at a top portion thereof, as illustrated in FIG. 15. It will be appreciated that the cable 12 is more securely gripped in the first position than in the second position.

The gripper frame 26.3 may typically comprise a planar strut. In other example embodiments, the gripper arrangement may comprise a triangular strut comprising wheels disposed at each corner thereof. In some example embodiments, the strut may be of varied geometric shapes.

The apparatus 10 also conveniently comprises drive means 30 configured to drive at least one of the wheels 26.1 and 26.2 of one or both gripper arrangement 26 of the links 16, 18 to rotate to move the apparatus 10 along the line 12. The drive means 30 may comprise one or more motors. It will be appreciated that a motor 30 may be provided for each of the wheels 26.1, 26.2 of each gripper arrangement 26. However, this need not be the case as a single motor 30 with high enough power and torque specifications may be configured to drive one or both of the wheels 26.1, 26.2 of one or both gripper arrangements, for example, by way of gears, pulleys, torque belts, etc. The drive means 30 may be configured to drive the wheels 26.1, 26.2 selectively. In some example embodiments each gripper arrangement 26 may have an associated motor to drive one or more of the wheels 26.1, 26.2, selectively.

It will be understood by those skilled in the field of invention that various example implementations may be envisaged to drive the apparatus 10 along the line 12. However, this should not detract from the wheels 26.1, 26.2 gripper arrangement 26 being driven by the drive means 30 to roll on the power line 12 thereby to move the apparatus 10 along the line 12 whether supported by both links with the grippers in any configuration, or in the serial link configuration with only a single gripper attached.

The apparatus 10 may be configured to traverse near-vertical slopes (such as on jumper cables), and also to traverse main spans as fast as possible. The drive means 30 may be selectable at least to realise this end.

It will be noted that the wheels 26.1, 26.2 may define a groove 32, at outer peripheries thereof. The circumferentially extending grooves 32 may be shaped and dimensioned to receive the line 12 substantially snugly therein thereby at least mitigating the risk of the apparatus 10 slipping on the line 12. In some example embodiments, traction means such as gripper formations or gripping material, such as rubber, may be disposed in the grooves 32 to reduce the risk of the apparatus 10 slipping on the line.

In a preferred example embodiment, the wheels 26.1, 26.2 are of differently matched sizes, particularly, the wheels 26.1, 26.2 are of different diameters such that which the same amount of power being supplied to both wheels 26.1, 26.2 by the drive means 30, one wheel 26.1 or 26.2 may advantageously provide more torque (at lower speed), for example, to enable vertical travel whereas the other wheel 26.2 or 26.1 may provide greater speed (at lower torque), for example, to enable relatively fast travel on a straight line traversal of the line 12.

Instead, or in addition, the above end may also be achieved via a gearbox.

In any event, the smaller wheel 26.1 is provided to engage a bottom portion of the cable 12 as it will not interfere with obstacles and will provide better contact force during gripping. The main drive wheel 26.2 is larger for better contact area.

The apparatus 10 may be operated to be driven on the line 12 when one or both of the gripper arrangements 26 grip the line 12. In addition, the apparatus 10 may be configured to be driven along the line 12 when the wheels 26.1, 26.2 are in the first engagement position as well as the second engagement position. Travel when the wheels 26.1, 26.2 are in the first position typically occurs when it is desired to grip the line more securely, e.g., travel on steep portions of the line 12. Travel when the wheels 26.1, 26.2 are in the second position typically occurs during normal or nearly horizontal traversing of the line 12 when more speed is required. The larger wheel 26.2 provides sufficient traction on the line in these instances.

It will be noted for brevity that five degrees of freedom are sufficient to provide attachment of the robot 10 to the cable 12 (moving onto a jumper cable). With two gripper joints, two link joints, and a core joint 20, five degrees of freedom exist in the serial manipulator (from the base to the end effector). However, since the base is mobile on the line (due to rolling capability of the gripper arrangement), this adds a redundant degree of freedom along the X0 axis of FIG. 3. In some example embodiments, at least one link joint 21 may be omitted while allowing for similar functionality as described herein. In the last mentioned example embodiment, the links 16, 18 may be connected via a core joint 20, a single link joint 21 adjacent either link 16 or link 18 as opposed to two link joints 21 and the core joint 20 as described above.

Essentially, the link joint redundancy makes it easier to keep the payload in the desired position, which is important when specifying the torque of the actuators in the design. The symmetry also makes individual control of joints more intuitive in some example embodiments. This makes the extra joint preferred over simpler manipulator kinematics.

Yet another degree of freedom which may be exploited to reduce the number of joints in the serial manipulator is the rotation about the X0 (line) axis. This degree is passive: it is not controlled directly by an actuator. However if the centre of mass of the machine is shifted along the Z0 axis (of FIG. 3) for example, then it is possible to control the position and orientation of the end effector using this degree of freedom. This rotation is typically measured by an accelerometer.

In any event, the apparatus 10 also comprises first image capturing means comprising a camera 38 configured at least to capture images of the line 12. The camera 38 is conveniently provided adjacent each gripper arrangement 26, for example, on the gripper frame 26.3. In this way, it will be appreciated that the manipulator link 16, 18, which is capable of movement in three dimensions, is conveniently configured to move the associated camera 38 correspondingly in three dimensions. Hence it is advantageously possible to inspect line 12 hardware from the viewpoint of any location in space which the manipulator link 16, 18 can achieve.

The apparatus 10 also conveniently comprises a control/processor arrangement or system 34 (FIG. 6) comprising one or more processors to control one or more operation/s of the apparatus 10. It is to be understood that the processor 34 may be one or more microprocessors, controllers, field programmable gate arrays (FPGAs) or any other suitable computing device, resource, hardware, software, or embedded logic. In addition, it will be noted that an image processing frequency of the processor 34 is selectable in order for the module 34 to control the links 16, 18 and the gripper arrangement 26 to grip and release the line 12. However, this configuration may be varied for different example embodiments.

The apparatus 10 may include a machine-readable medium, e.g. memory 36 in the processor 34, main memory, and/or hard disk drive, which carries a set of instructions, or embedded software/code, to direct the operation of the processor 34.

It will be understood that the processor 34 is described to include a plurality of modules which correspond to the functional tasks to be performed by the processor 34. In this regard, "module" in the context of the specification will be understood to include an identifiable portion of code, computational or executable instructions, data, or computational object to achieve a particular function, operation, processing, or procedure. In some example embodiments, it will be appreciated that a module need not be implemented in software; a module may be implemented in software, hardware, or a combination of software and hardware. Further, the modules need not necessarily be consolidated into one device but may be spread across a plurality of devices.

In particular, the processor 34 may comprise a navigation module 40 configured to receive the captured images from the camera 38 associated with the respective manipulator link 16, 18. The module 40 is also able to process received captured images to determine the configuration of the robot or an orientation or configuration of the respective link 16, 18 and/or gripper arrangement 26 relative to the cable 12 and also to control the links 16, 18 and the gripper arrangement 26 to grip or release the line 12.

In particular, the module 40 is configured to process the received captured images by applying an algorithm for tracking the power line. It will be noted that the navigation module 40 may be configured to receive data from one or more of a global positioning system, an inertial platform, and an inspection system (mentioned below). The module 40 may then process received captured images to determine the configuration of the robot 10; and control the links 16, 18 and the gripper arrangement 26 to grip, or release, the cable 12, in use.

In one example embodiment, instead or in addition to the processing methodologies described herein, the module 40 is configured to perform its image processing on a small "region of interest" (ROI), which reduces computation time. Considering that the camera field of view is small relative to the length of the line 12, the line 12 should span across the entire field of view as long as the camera 38 is pointed at the line 12. Processing an ROI around the border of the image should return two regions where the conductor strand pattern is detected. Since the conductor 12 is essentially straight (over short lengths in the case of a jumper) the two regions may be used to infer the region that the cable 12 takes up in the image.

The ROI may be any shape. In this example embodiment, the ROI is a ring that allows the orientation of the line to be found without directly applying trigonometry. The ROI is initialised using sine and cosine operators, with the pixel positions of the ROI being stored in a lookup table, along with the angles used to calculate those positions.

Figure 7:
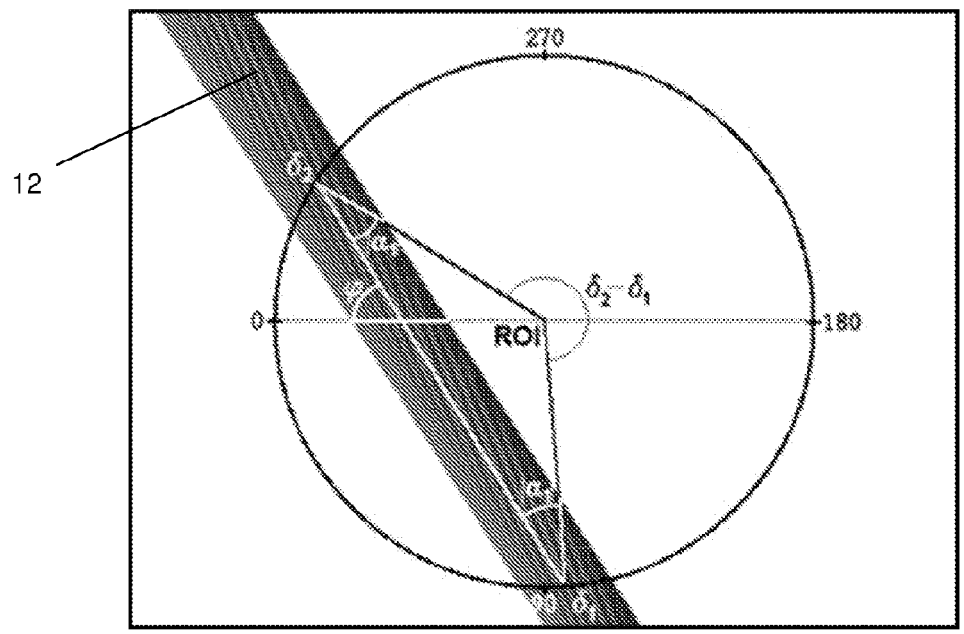
FIG. 7 shows a rendered image of a power cable with a region of interest (ROI) overlay and angle detection geometry in accordance with an example embodiment.

As illustrated in FIG. 7, the line connecting the centroid of the two strand patterns found on the ROI, is a chord (by definition). The endpoints of the chord correspond to the angles $\delta_1$ and $\delta_2$, which are referenced from the ROI lookup table. Using elementary geometry, these angles are all the data required to determine the chord's angle relative to the horizontal, $\phi$. The chord angle, and hence the conductor angle, is $$\phi = 180 - \delta_1 - a_1 \qquad (1)$$

where $a_1 = ((\delta_2 - \delta_1) - 180)/2$ and $|a_1|$ is the magnitude of the base angles of the isosceles triangle shown in FIG. 7.

The ROI data extracted from the image is one pixel wide, and $\pi d$ long, where d is the diameter of the ROI in pixels.

Figure 8:
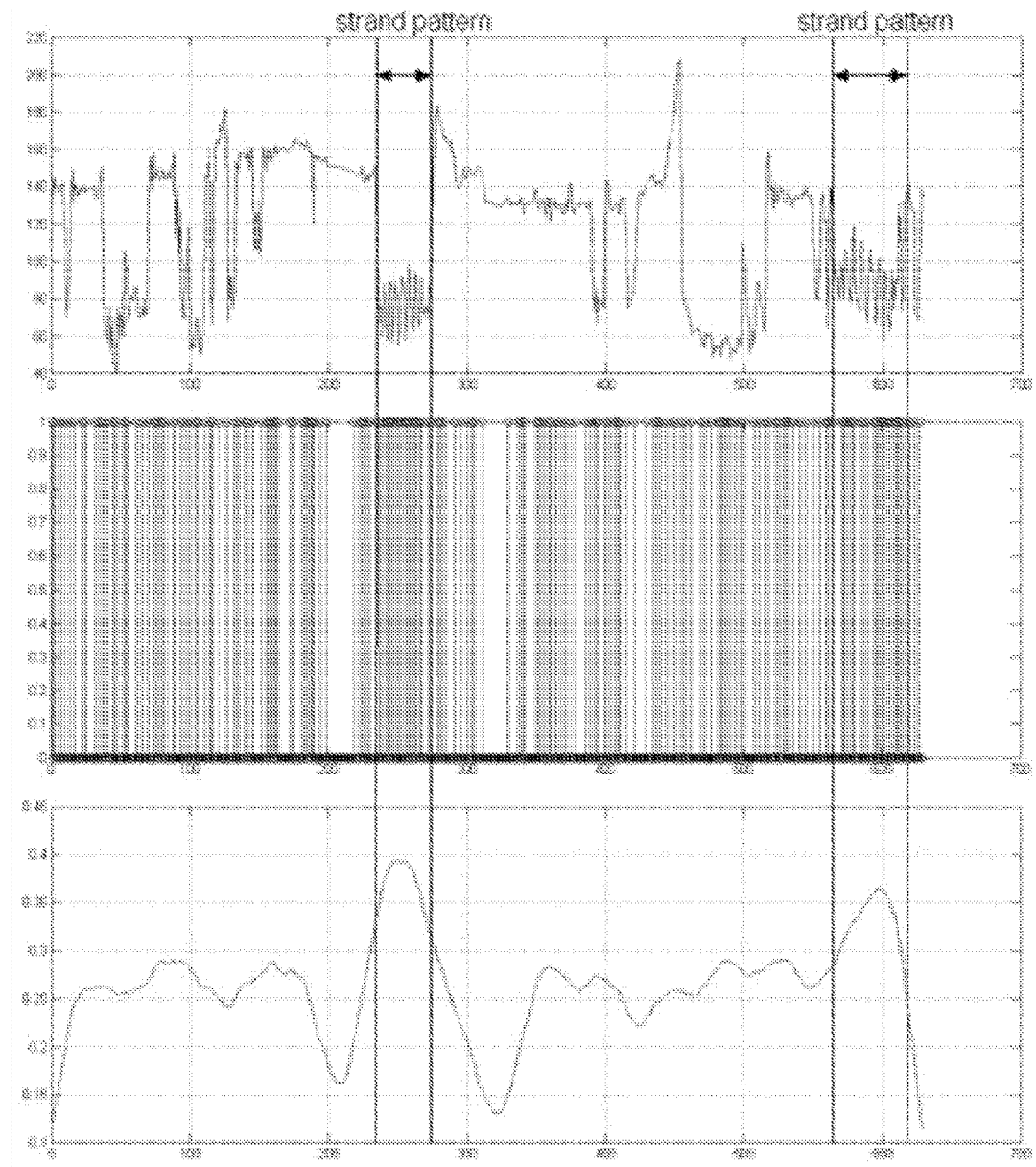
FIG. 8 shows graphs of ROI grey level, "edge" detection, and averaging in accordance with an example embodiment.
Figures 13, 14:
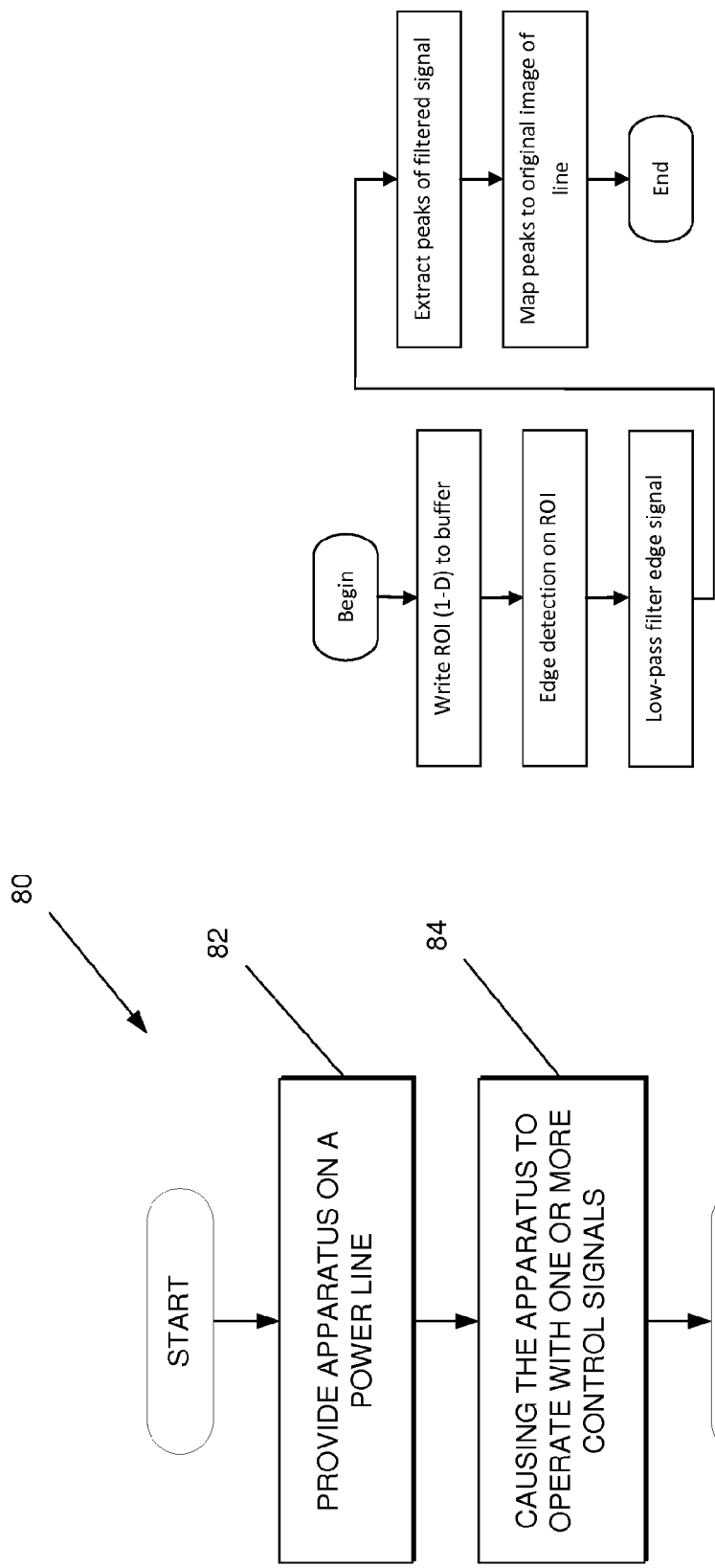
FIG. 13 shows a high level flow diagram of a method in accordance with an example embodiment.
FIG. 14 shows a flow diagram of a method for finding the line using image processing.

The ROI data may be thought of as a signal, as shown in the first graph of FIG. 8. In this example embodiment, two filtering operations are performed on the signal by the module 40 to find the strand patterns. Firstly, the module 40 is configured to apply a high-pass filtering operation to highlight greyscale rate of change. The filter output is thresholded and normalised, in much the same way that edge detection is performed on a 2-D image. This is shown in the second graph of FIG. 8. Secondly, the module 40 is configured to apply an averaging filter operation to smooth the signal, so that the centres of the densest regions of "edges" become signal maxima, as shown in the third graph of FIG. 8. The two largest maxima are taken to be the centres of the strand patterns, and the position of the line is inferred using the ROI lookup table stored in memory 36. These operations of the module 40 are illustrated in FIG. 14 (mentioned briefly below). The module 40 is therefore configured to use the inferred position of the line to control the links 16, 18 and the gripper arrangement 26 to locate the line 12 in the locating zone 28. The gripper arrangement 26 may be operated to rotatably grip the line 12 as hereinbefore described.

Figure 9:
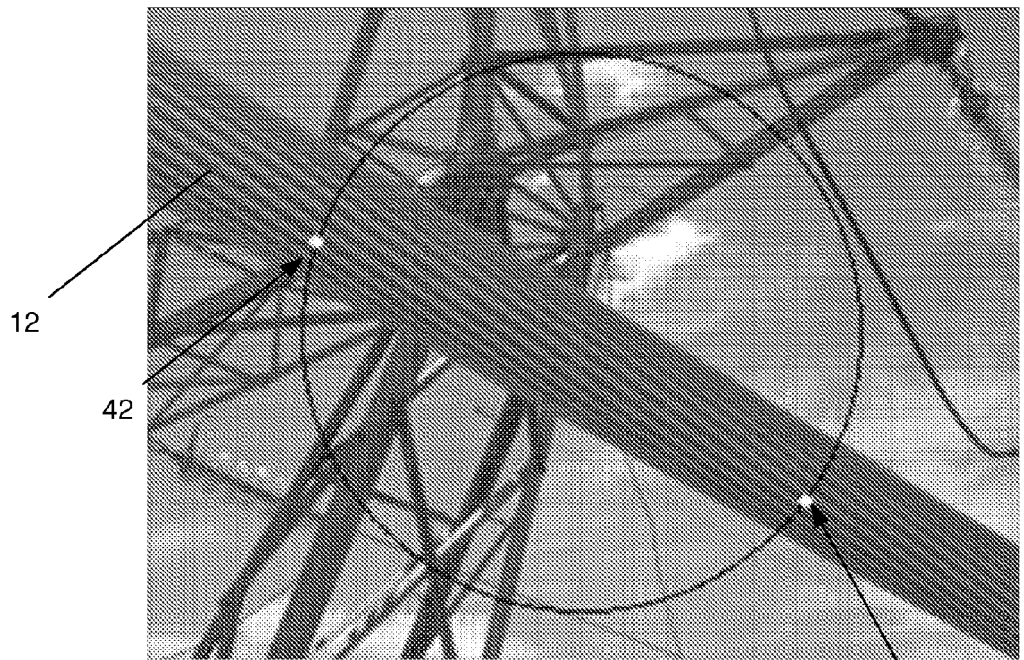
FIG. 9 shows a composite image showing ROI mapped maxima in accordance with an example embodiment.

FIG. 8 illustrates the filtering operations for an ROI off a composite image and FIG. 9 shows an image of a conductor 12 rendered over a photograph taken near a tower, to simulate a "real-world" background together with line detail expected from the apparatus's camera 38. The two largest maxima in the third graph of FIG. 8 are mapped to FIG. 9 as white dots 42.

Similarly, the processor 34 may comprise an obstacle avoidance module 44 configured to receive captured images of the cable 12 and other sensor inputs and to process these data to determine whether an obstacle is in the path of the apparatus 10 on the cable. The module 44 is configured to control one link 16, 18, joint 20 and gripper arrangement 26 to operate as an end effector and bypass the obstacle and to engage the cable 12 at another zone thereof, typically beyond the obstacle. The corresponding base gripper arrangement 26 is then operated to disengage from the cable 12 and reattach to the same at a zone past the obstacle for conventional travel along the cable 12.

It will be noted that the obstacle avoidance module 44 may operate substantially in a similar manner as the module 40. In particular, the modules 40 and 44 may work in tandem to allow the link 16, 18 to engage the cable 12 at the zone beyond the obstacle.

It will be understood that the apparatus 10 may comprise one or more of inspection and maintenance systems. In a preferred example embodiment, the inspection system may comprise a second image capturing means comprising an inspection camera 45 also to capture images of the cable 12 from a different perspective. It will be noted that in some example embodiments, the images processed by the modules 40 and 44 may comprise images captures by the camera 45. Camera 45, and 38 for that matter, may be configured to capture high resolution images to enable ease of remote inspection of the cable. The second camera 45 may be provided at the body 14. Camera 38 is conveniently able to capture desired images which may be obscured from the line of sight of the second main inspection camera 45.

The inspection system may comprise a measurement system to obtain and process data to obtain electrical, magnetic and electromagnetic data associated with the line 12 as will be described below.

Figure 10:
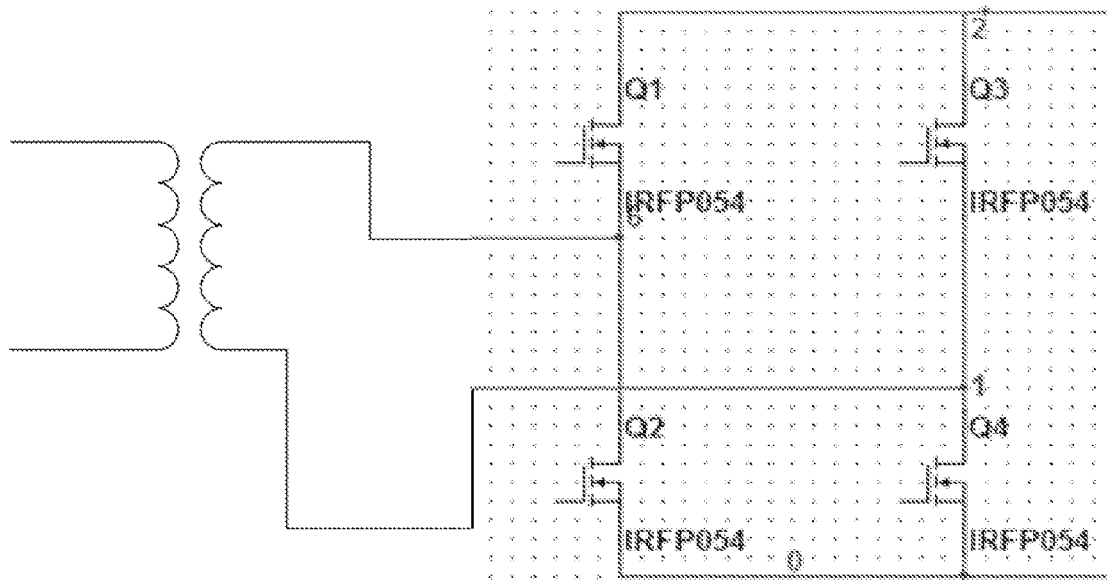
FIG. 10 shows an example illustration of a transformer arrangement in accordance with an example embodiment.

In a preferred example embodiment of the invention, the apparatus 10 comprises a power module to power the apparatus 10 and all or most of the electrical components associated therewith. Though in some example embodiments, the power module may comprise a replaceable and/or re-chargeable battery pack. Instead, or in addition, the power module comprises a transformer arrangement 46 to draw current from the line 12 to power the apparatus 10. To this end, the transformer arrangement 46 may comprise a split core means 46.1 attachable to a frame and at least partially enclosing the line 12 with the possibility of an adjustable air gap 46.2 provided. It will be noted that the split core means 46.1 may comprise a ring controllable electrically, or mechanically, to open to two semi-circular halves to receive the power line 12 therein. It will be understood that the means 46.1 may be of any shape to enclose the line 12. The means 46.1 is controllable electrically, or mechanically, to close to provide a ring around the line 12 with a gap 46.2 (as illustrated in the Figures) thereby to supply the apparatus 10 with, for example, DC voltage, e.g., by way of the circuit configuration illustrated in FIG. 10 which combines prior art of a boost convertor and a controlled synchronous rectifier bridge. The split core means 46.1 conveniently may double as a safety hook when in the closed position to prevent the apparatus 10 from falling from the line 12, for example, as a result of wind, vibration, or shock loading during normal transverse motion along the line while the gripper arrangements 26 are in the open position (as in FIG. 15).

The DC voltage generated by the transformer arrangement 46 may be used to charge a backup power battery associated with the apparatus 10 for instances where insufficient current flows through the line 12 or when the apparatus 10 has high instantaneous current demand.

The processor 34 may comprise a measurement determining module 48 configured to receive data from, or associated with, at least the transformer arrangement 46 and to determine one or more electrical, magnetic and electromagnetic properties associated with the line 12. The data received from the transformer arrangement 46 may comprise signal data and measurements which may be obtainable from the transformer arrangement 46 and/or one or more electronic measurement devices.

In particular, the transformer arrangement 46 may be used by the module 48 to measure the primary line current which may, for example, be of use to determine the splice resistance or the current sharing in a particular sub-conductor in a bundle. To this end, the power supply transformer 46 may be configured to be opened to have a well defined air-gap 46.2 to enhance its utility for current measurement because of the nearly linear relationship between magnetic field intensity and magnetic flux density. The current measurement may be achieved using a method similar to an air cored Rogowski coil where the secondary EMF is be integrated numerically by way of the module 48, or via analogue circuits, and the result is manipulated to obtain a measure of the primary current. Examples of some equations for these calculations are as follows:

$$N_1 i_1 = H_c l_c + H_g l_g$$

$$e_2 = A N_2 \frac{dB}{dt}$$

Where B is the magnetic flux density in Tesla; H is the magnetic field intensity in Ampere-turns per meter; l is length in meters; subscript c refers to the core and subscript g refers to the gap; and subscripts 1 and 2 refer to the primary and secondary sides of the transformer respectively.

An alternative is to measure the magnetic flux density directly by way of suitable measurement electronics, for example, a Hall-effect device, and manipulate this by processing data associated therewith with the module 48 to obtain a measure of the primary current When opened, the transformer arrangement 46 may be used to deduce the local magnetic field strength.

Figure 11:
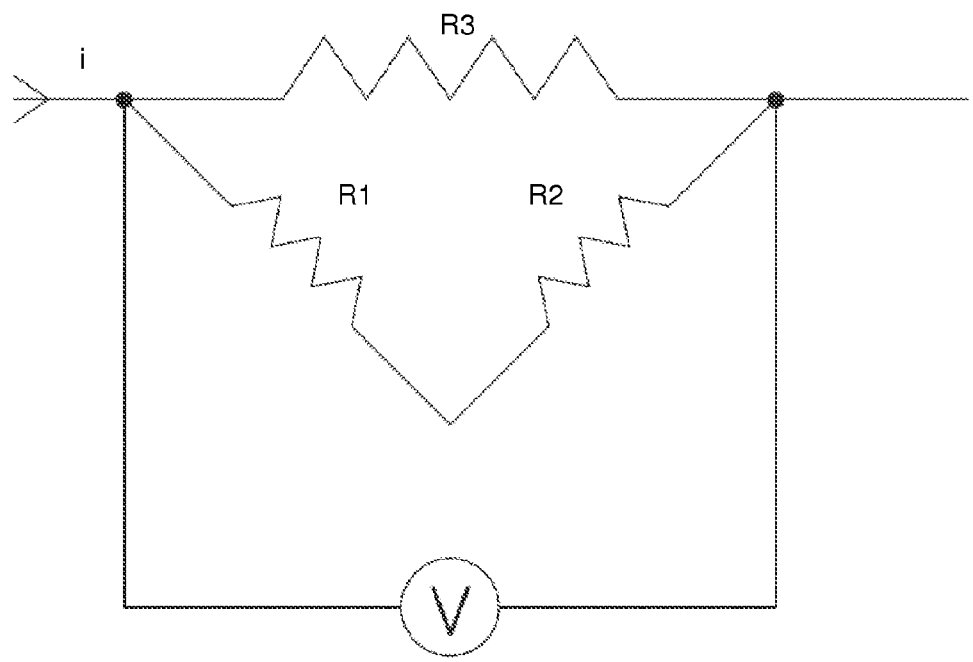
FIG. 11 shows an example illustration of a resistance profile measurement using the apparatus of FIG. 1 on the power cable in accordance with an example embodiment.

It will be appreciated that each link 16, 18 may comprise electrically resistive portions 50 (FIG. 2, illustrated conceptually), thereby to enable the measurement determining module 48 to determine a voltage drop across a span of the two links 16, 18 when both grip the line 12. This may be done, for example, as part of measuring electrical resistance of a splice (between the two links 16, 18) in conjunction with a current measurement. In this configuration, the apparatus 10 would form a parallel resistive circuit of known resistance that would be taken into consideration when evaluating the splice resistance as illustrated in FIG. 11. R1 and R2 are resistances associated with the links 16 and 18 and R3 is the resistance associated with the splice.

In addition to the resistive portions 50, the links 16, 18 may comprise electrical fuse portions 52 (FIG. 2, illustrated conceptually). The electrical fuse portions 52 advantageously act as a failsafe mechanism, should the apparatus 10 operate out of the electrical clearance window of line 12 to which it is attached and become the source of a short circuit.

The links 16, 18 may include a resistive probe (not illustrated) to facilitate charging the apparatus 10 to a potential of the line 12 and to discharge the apparatus to the earth potential during placement and removal of the apparatus 10 from the line 12.

The apparatus 10 also advantageously comprises a communication means 54 configured to enable the apparatus 10 to receive and transmit data. In particular, measurements obtained and images captured by the apparatus 10 may be transmitted wirelessly via the module 54 to a remote operator or station for inspection and analysis. This may also be done by the apparatus 10 (autonomously), which logs any faults and sends a report to the ground station or stores the same for download at a later time. Similarly, it will be appreciated that the apparatus 10 may be configured to receive control signals to control operation of the apparatus 10. In this regard, the control signals received by the module 54 may be processed by the processor 34 which controls the apparatus 10 accordingly.

Figure 6:
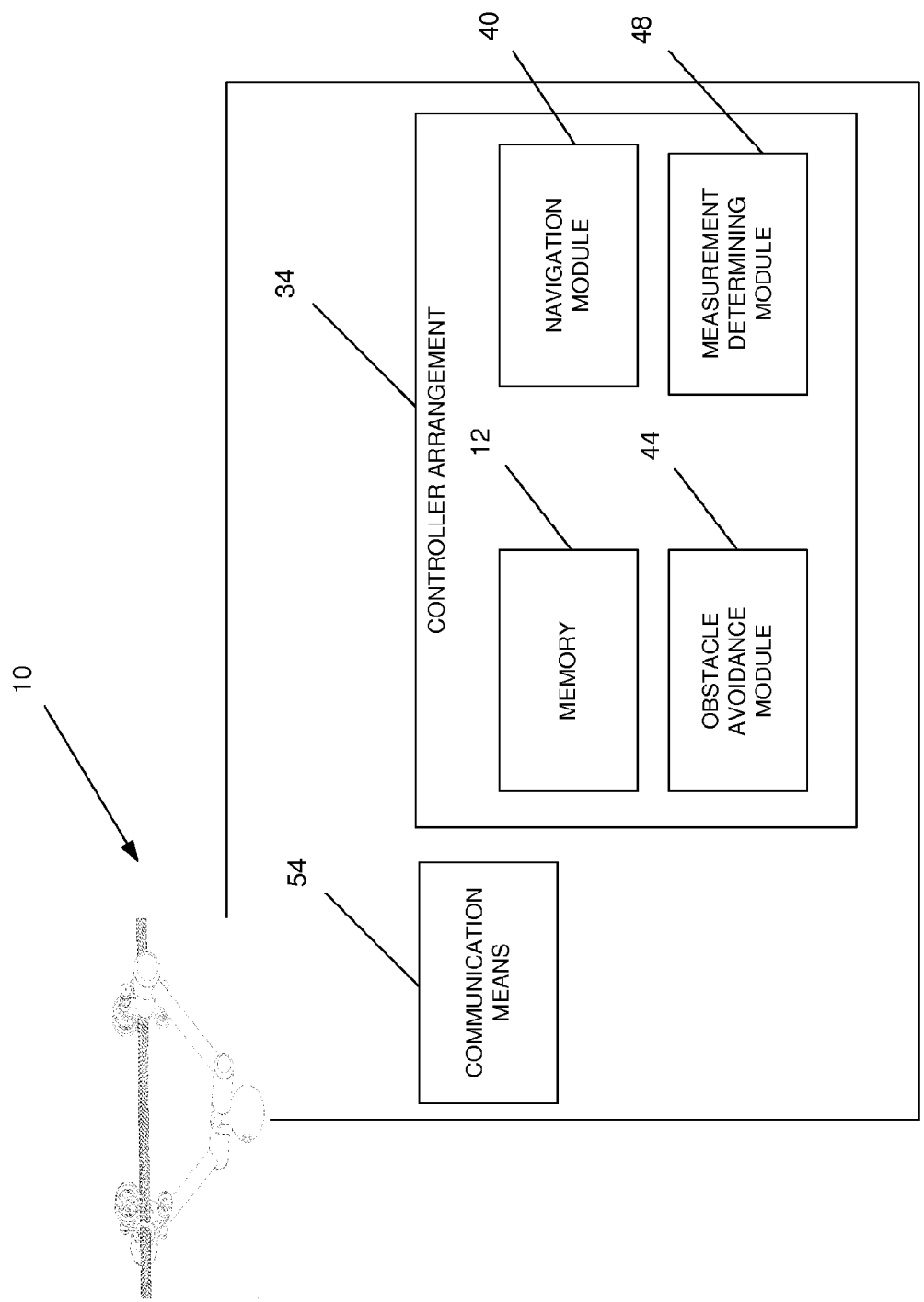
FIG. 6 shows a schematic block diagram illustrating some of the components of the apparatus of FIG. 1 in accordance with an example embodiment.

The components such as those illustrated in FIG. 6, as well as the camera 45, may be provided in the payload body 14. For succinctness, no detailed description is provided for various electronic components of some of the parts of the apparatus 10, e.g., drivers, certain discrete measurement circuitry, etc. However, these are well understood by those skilled in the art and no further mention will be made of the same.

Figure 12:
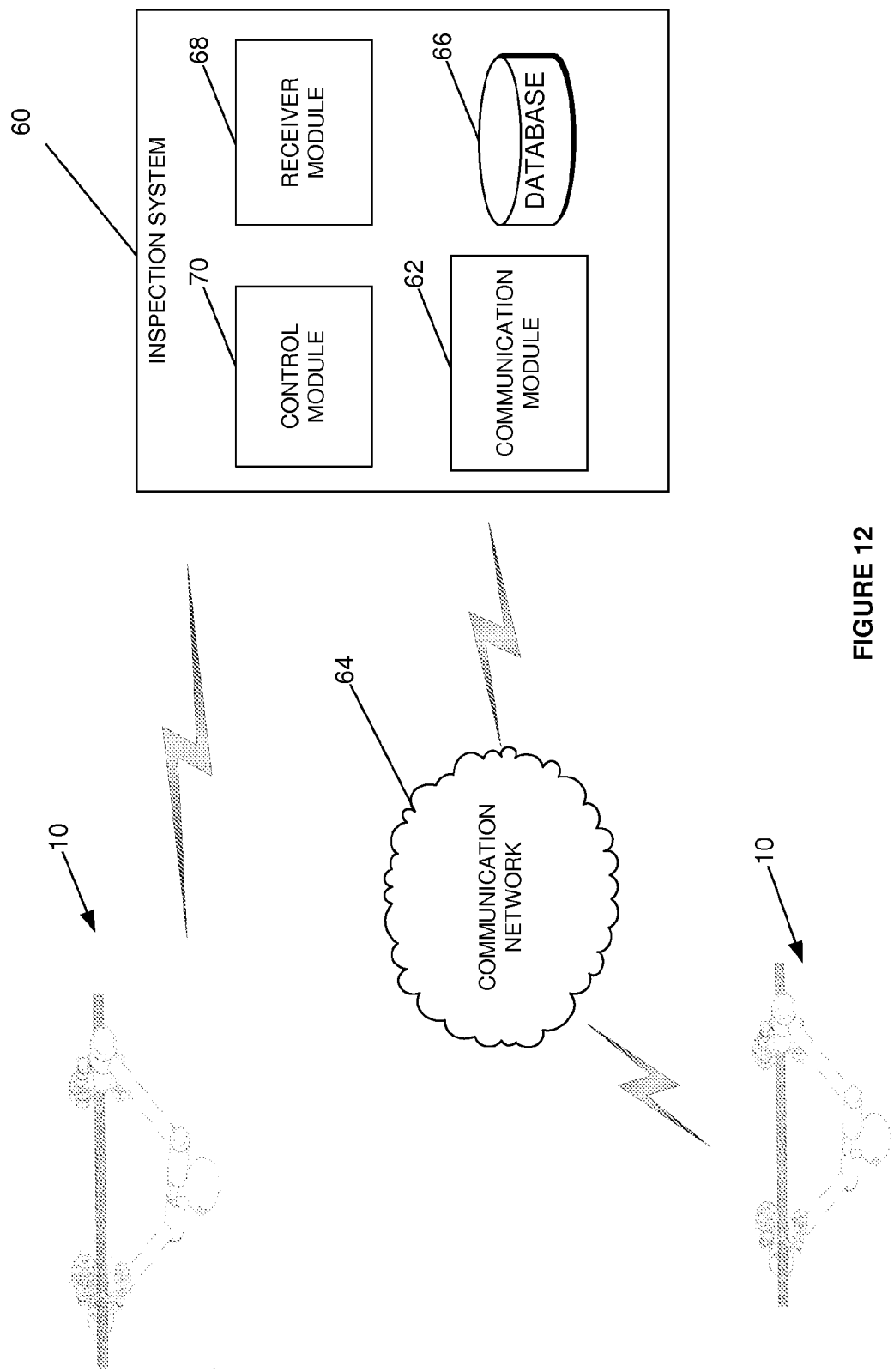
FIG. 12 shows a schematic diagram illustrating an inspection system in accordance with an example embodiment.

Referring to FIG. 12 of the drawings where a system of inspecting a cable or power line 12 is generally indicated by reference numeral 60.

The system 60 comprises, or is in communication with, a plurality of apparatuses 10 in accordance with the invention. The system 60 may be provided at least partly at a computing device, e.g., a personal computer at a remote location to the apparatuses 10 or may be provided on a mobile computing device operable by a human operator proximate the apparatuses 10, or both.

In any event, the system 60 comprises a communication module 62 configured to receive data from the apparatuses 10 via a communication network 64. The communications network 64 may be a wireless communication network 64 such as a cellular telecommunications network. The network 64 may further comprise a packet-switched network and may form part of the Internet. Instead, the communications network 64 may be a circuit switched network, public switched data network, or the like.

It will be appreciated that the system 60 may be communicatively coupled with the apparatus 10 via a short range wireless technology, such as Bluetooth, or the like.

The system 60 comprises a database 66 for storing data. The system 60 further comprises a receiver module 68 configured to receive one or more signals comprising data from at least one apparatus 10. The system 60 may comprise or may be in communication with a plurality of apparatuses 10. However, only two are shown for ease of illustration.

The system may comprise a control module 68 operable to generate and transmit, via the communication module 62, one or more command signals to the apparatus 10, wherein the control signals are configured to control the apparatus 10. The control module 68 may allow an operator to operate the apparatus 10 in a fully remote control manner. Instead, or in addition, the control module 68 may be configured to prompt the apparatus 10 to transmit data or to follow a particular course, for example, the processor 34 may be configured to receive the control signal and perform a particular course correction or obstacle avoidance manoeuvre depending on the signal received. In certain example embodiments, it will be appreciated that the apparatus 10 is completely autonomous once on the line 12.

It will be appreciated that the apparatus 10 may be operable to capture images and other signals (GPS location, orientation, right of way clearances, temperature, resistance, acoustic noise, etc.) These may be processed on-board or off-line to generate a report that will highlight anomalies or points of concern and to provide a record of the current state of the line. The information may be captured into a GIS system to provide a historical record of the state of the line by location.

The movement of data from the on-board system to any off-board system may be by any means including wireless or wired connection.

In use, referring to FIGS. 1 to 17 of the drawings, the apparatus 10 is conveniently stored in a stowage position as illustrated in FIG. 4 where the links 16, 18 are substantially parallel to each other. When it is desired to be used, the apparatus 10 is removed from the stowage position by the operator.

At this stage, it will be noted that method 80 of FIG. 13 may be carried out, wherein the apparatus 10 is provided, at block 82, on the line 12 to be inspected. In particular, the apparatus 10 is attached to the power cable or line 12, typically from a support tower associated therewith, by a human operator. The links 16, 18 are both are operatively attached to the line by way of respective gripper arrangements 26. In the illustrated example embodiment of FIG. 15, the apparatus 10 is operatively attached to the line with the gripper arrangements in the second engagement position with only one wheel 26.2 of each gripper arrangement 26 attached to the top of the line such that the line 12 is snugly in the groove 32. This configuration, as mentioned above, is typically used when the apparatus 10 is traversing large or straight lengths of line 12 where there is minimal risk of the apparatus 10 falling from the line 12.

Figure 16:
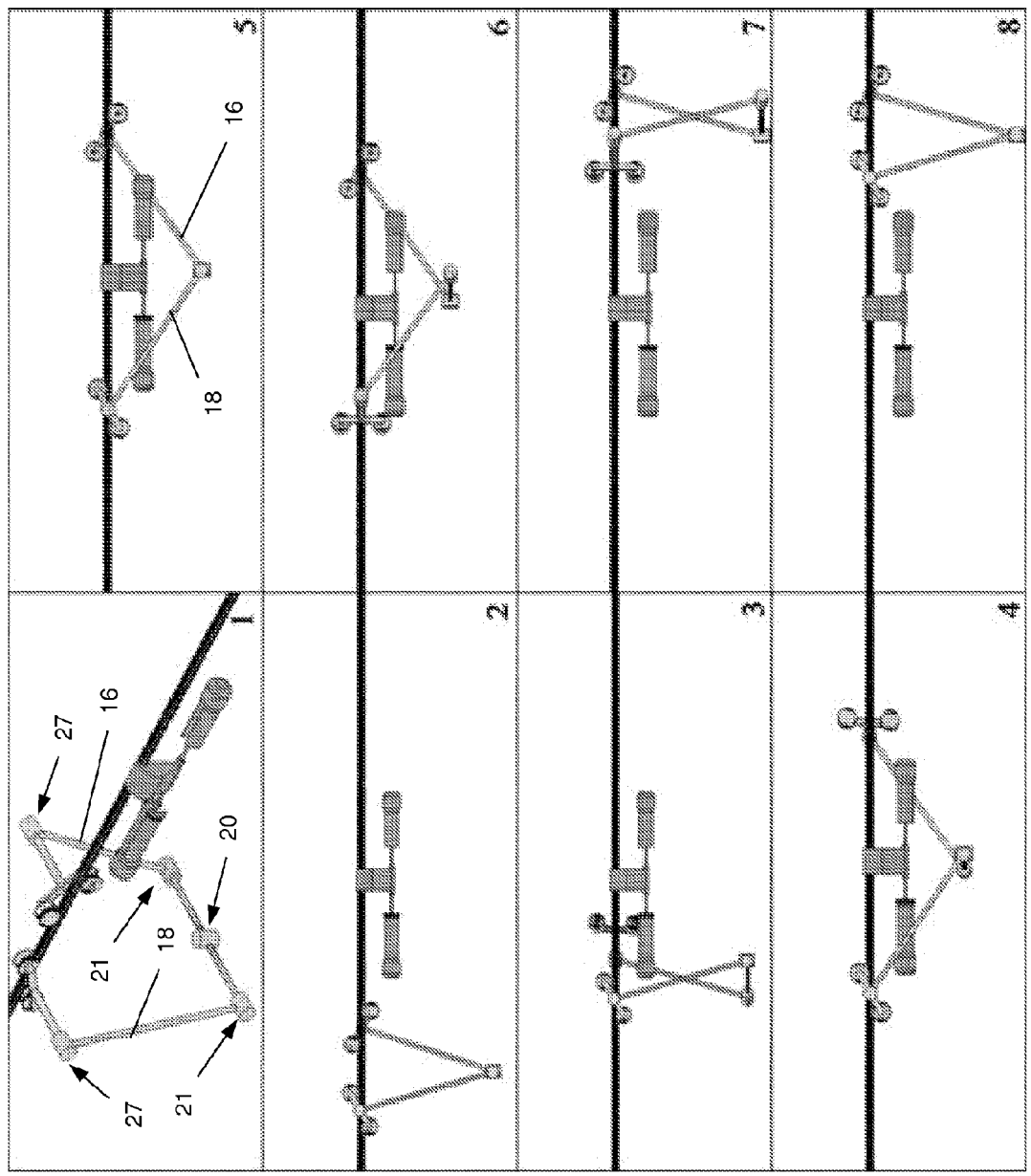
FIG. 16 shows an illustrative operational process flow diagram of an apparatus in accordance with an example embodiment, in use, performing a damper negotiation on a line in accordance with an example embodiment.

By way of example, for performing obstacle negotiation, reference is made particularly to FIG. 16 of the drawings, wherein the apparatus 10 in accordance with the invention hangs beneath the line 12. It approaches obstacles with its gripper arrangements 26 close together, in frame 1. The front gripper arrangement 26 of, for example, link 16 is actuated by the joint 27 to disengage from the cable 12, and the core joint 20 and/or the link joint/s 21 is/are actuated to move link 16 away from the obstacle, in frame 2. The apparatus 10 drives forward on the line via wheels 26.1 and 26.2 of the still attached gripper arrangement 26 of the link 18, or in other words the base, so as to get the rear gripper arrangement 26 of the link 18 as close to the obstacle as possible, in frame 3. The link joints 21 are actuated so that the reach of the apparatus 10 is extended, in frame 4 as the links 16,18 displace relative to each other scissor fashion. Once the front gripper arrangement 26 of the link 16, or in other words the end effector, is beyond the obstacle, frame 5, it is operated via joint 27 to grip the cable 12. Frame 6, the rear gripper arrangement 26 of link 18 or the base detaches and is moved away from the line 12 as an end effector wherein the gripper arrangement 26 of the link 16 now serves as a base. Frame 7, the link joints 21 are operated such that links 16, 18 retract the reach of the apparatus 10, and the apparatus 10 drives forward. Frame 8, the rear gripper arrangement 26 of link 18 or the end effector is operated to grip the cable, and the obstacle is cleared.

Figure 17:
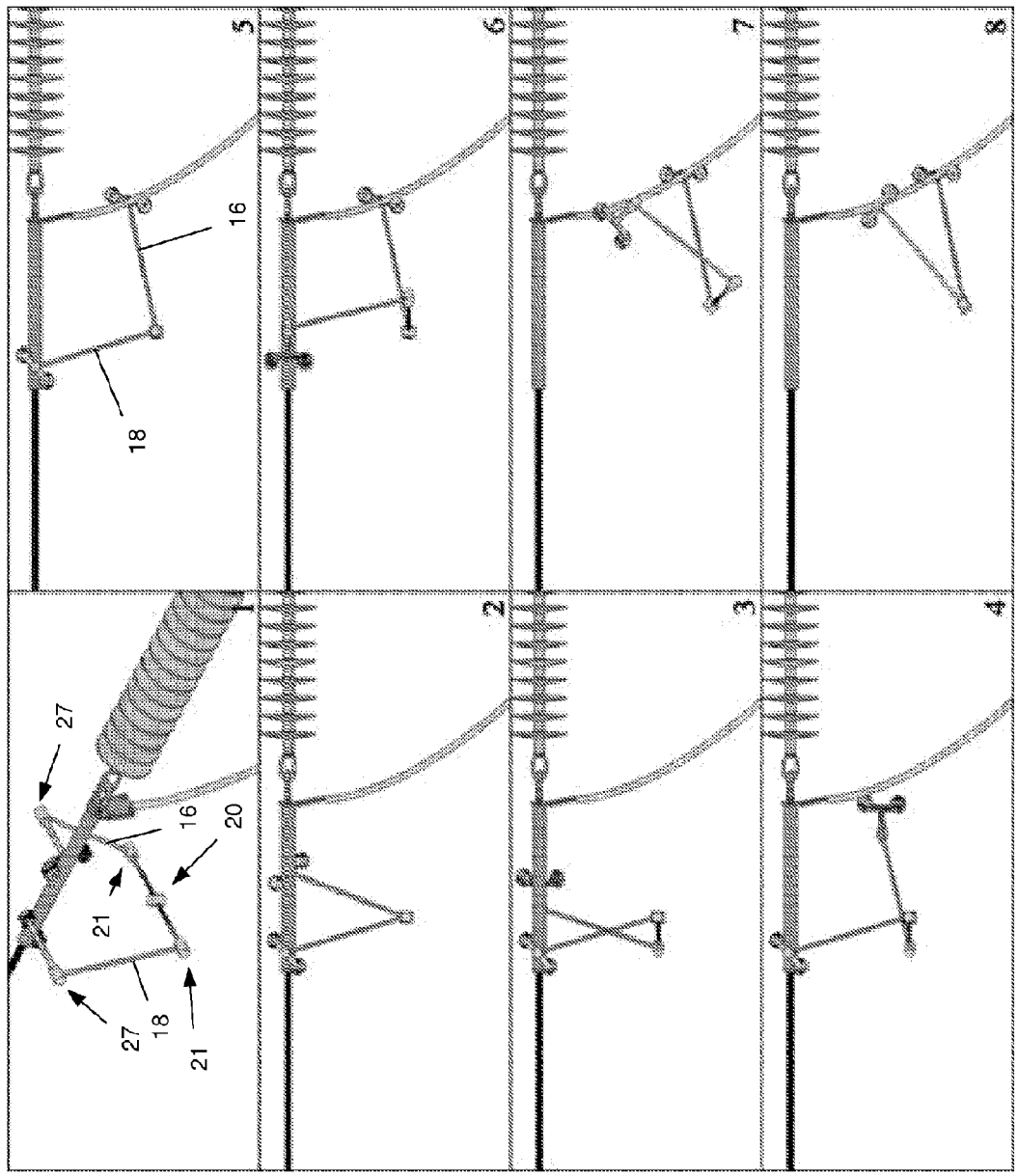
FIG. 17 shows an illustrative operational process flow diagram of an apparatus in accordance with an example embodiment, in use, performing a jumper negotiation on a line in accordance with an example embodiment.

By way of another example, for performing jumper negotiation, reference is made particularly to FIG. 17 of the drawings. In FIG. 16, as with obstacle negotiation described above, in Frame 3, the front gripper arrangement 26 of the front link, for example, link 16 releases the cable and is moved away from the line 12 as its first step to attaching to the jumper cable as an end effector. In frame 4, the front link 16 is rotated via joints 20 and/or 21 to move the front gripper arrangement 26 thereof into proximity with the cable 12. In frame 5, the core joint 21 brings the gripper arrangement 26 of link 16 into alignment with the cable 12, and the gripper arrangement 26 of link 16 is operated to grip the cable 12. In frame 6, the rear gripper arrangement 26 of link 18 serving as a base releases the line 12 and serves as end effector to the base which is now the attached gripper arrangement 26 of the link 16, and the apparatus 10 is able to, in frame 7, move down the jumper. The rear link 18 (via the link joints 21 and/or core joint 21) brings the detached gripper arrangement 26 thereof into proximity with the jumper, and then, at frame 8 the core joint 20 brings the gripper arrangement 26 into alignment with the jumper. The gripper arrangement 26 of the link 18 as end effector is then operated to grip the cable 12.

In any event, the operator or associated automation system will also operate the transformer arrangement 46 such that the split core means 46.1 partly closes around the line 12. It will be appreciated that the means 46.1 may optionally be controlled, either manually or automatically, to disengage from its position around the line 12, e.g., once the apparatus 10 is fully charged, or if the links 16, 18 are to be disconnected from the line 12. Once on the line, it will be appreciated that the method 80 comprises causing, at block 82, the apparatus 10 to operate. This may be done by way of a control signal generated by the module 70, and transmitted wirelessly via the module 62, and receivable by the processor 34 via the communication means 54. In some example embodiments the control signal may be given once the apparatus 10 is powered or once it is switched on.

Further in use, it will be appreciated that the motor 30 may drive the wheel 26.2 of each gripper arrangement 26 along the line 12. When the apparatus 10 requires to grip the line 12 more securely, for example, in the case of a steep gradient in the line 12, the revolute joint associated with each gripper arrangement 26 is operated such that the gripper frame rotates in the direction of arrows 29 (either clockwise or anti-clockwise) to bring the wheel 26.1 also into engagement with the line 12, typically at a bottom portion thereof, such that the gripper arrangement 26 is in the second engagement position wherein the line 12 is gripped between the wheels 26.1, 26.2 and is held in place in the grooves 32, as illustrated in FIG. 5. While wheels 26.1, 26.2 engage opposite sides of the line 12, it will be noted that they may still be driven by the motor/s 30 to cause the apparatus 10 to move along the line 12. In this way, the apparatus 10 is configured advantageously to firmly grip the line 12 in a selective manner and also travel simultaneously thereon, if desired.

While travelling along the line, or stationary at a desired location on the line, it will be appreciated that when the second portions 16.2, 18.2 are parallel and substantially in line with each other, the singularity configuration described above is achieved and the payload body 14 may be moved from a position as illustrated in FIG. 1 to a position illustrated in FIG. 2 such that the camera 45 is directed at the line 12 to which the apparatus 10 is attached to. The camera 45 may be operated to capture images of the line 12. To this end, the camera 45 may typically have its own pan and tilt actuation. It will be noted that the images may be transmitted wirelessly from the apparatus 10, e.g., to the receiver module 68 of the system 60. Instead, or in addition, the images may be processed and/or stored on-board.

In addition, the measurement determining module 48 may be operated to determine various electrical measurements associated with the line, such as, splice resistance, current flowing, associated voltage of the splice, or the magnetic/electromagnetic characteristics associated therewith as hereinbefore mentioned. In summary, the apparatus 10 may be configured to perform one or more of electrical, mechanical, acoustic, thermal, and right of way inspection by way of appropriate means and/or sensor arrangements.

If desired, or if the apparatus 10 encounters an obstacle on the line 12 (which may be any one of a wide range of obstacles which prevent the apparatus 10 from travelling on a straight portion of the line 12, e.g., at an intersection between a jumper cable and a main line 12), the split core means 46.1 may be opened, if not already opened, such that it unhooks from the line 12. If the gripper arrangement 26 is not in the second engagement position, the apparatus 10 is operated to rotate the gripper frame 26.3 and hence wheels 26.1, 26.2 of one gripper arrangement 26, for example, of link 16 to grip the line 12 in the first engagement position (as illustrated in FIG. 5). The gripper frame 26.3 and hence wheels 26.1, 26.2 of the other link 18 is then rotated to release the line 12 therefrom such that the link 18 is free to move relative to the line 12 (via the joints 20 and 21) with gripper arrangement 26 of the link 18 being the end effector relative to the base (attached gripper arrangement 26 of link 16). The module 44 may be operated such that the link 18 bypasses the obstacle and attaches to the line 12 at a zone beyond the obstacle, or a desired zone within reach of the end effector.

It will be appreciated that when the obstacle is bypassed and the gripper arrangement 26 of the link 18 needs to attach to the line 12 once more, the module 40 is operated in a manner as hereinbefore described with reference to FIG. 14. Once the line 12 is in the cable locating zone 28, the gripper arrangement 26 is operated such that the gripper frame 26.3 is rotated thereby allowing the wheels 26.1, 26.2 to engage and grip the line 12 on opposite sides thereof in the first engagement position.

In a similar fashion, the module 44 the controls the base gripper arrangement 26 of link 16 to disengage from the line 12, effectively being the end effector where the gripper arrangement 26 of the link 18 attached to the line is the base link. The link 16 is then controlled to move beyond the obstacle and to attach (via its gripper arrangement 26) to the line 12 at a region adjacent the link 18. In some example embodiments, the link 16 may move to a location beyond the link 18, in the direction of travel.

Once past the obstacle, the wheels 26.1, 26.2 of the gripper arrangement 26 may be driven by the motor/s 30 to move along the line 12 while still in the first engagement position. However, it will be noted that the gripper arrangement 26 may be operated to rotate such that only one wheel 26.1 or 26.2 is provided on the line 12 and driven by the motor/s 30 i.e. such that the wheels 26.1, 26.2 are in the second engagement position.

The present invention provides an apparatus for use on a power line which conveniently addresses problems associated with conventional line inspection systems. The apparatus 10 in accordance with the invention provides a more dynamically ambidextrous apparatus for use on cable.

As mentioned above, the singularity configuration as hereinbefore described allows for the payload body 14 positions to be changed without affecting the manipulator (all the links between the attached link 16, 18 and the detached link 18, 16) position; this is advantageous as some conventional machines comprise mechanisms purpose-built to move the payload bodies relative to the rest of the structure. Shifting the payload body 14 in the manner provided in the present invention allows for the adjustment of weight distribution on the wheels, as well as the loading on other joints to be controlled.

Figure 18:
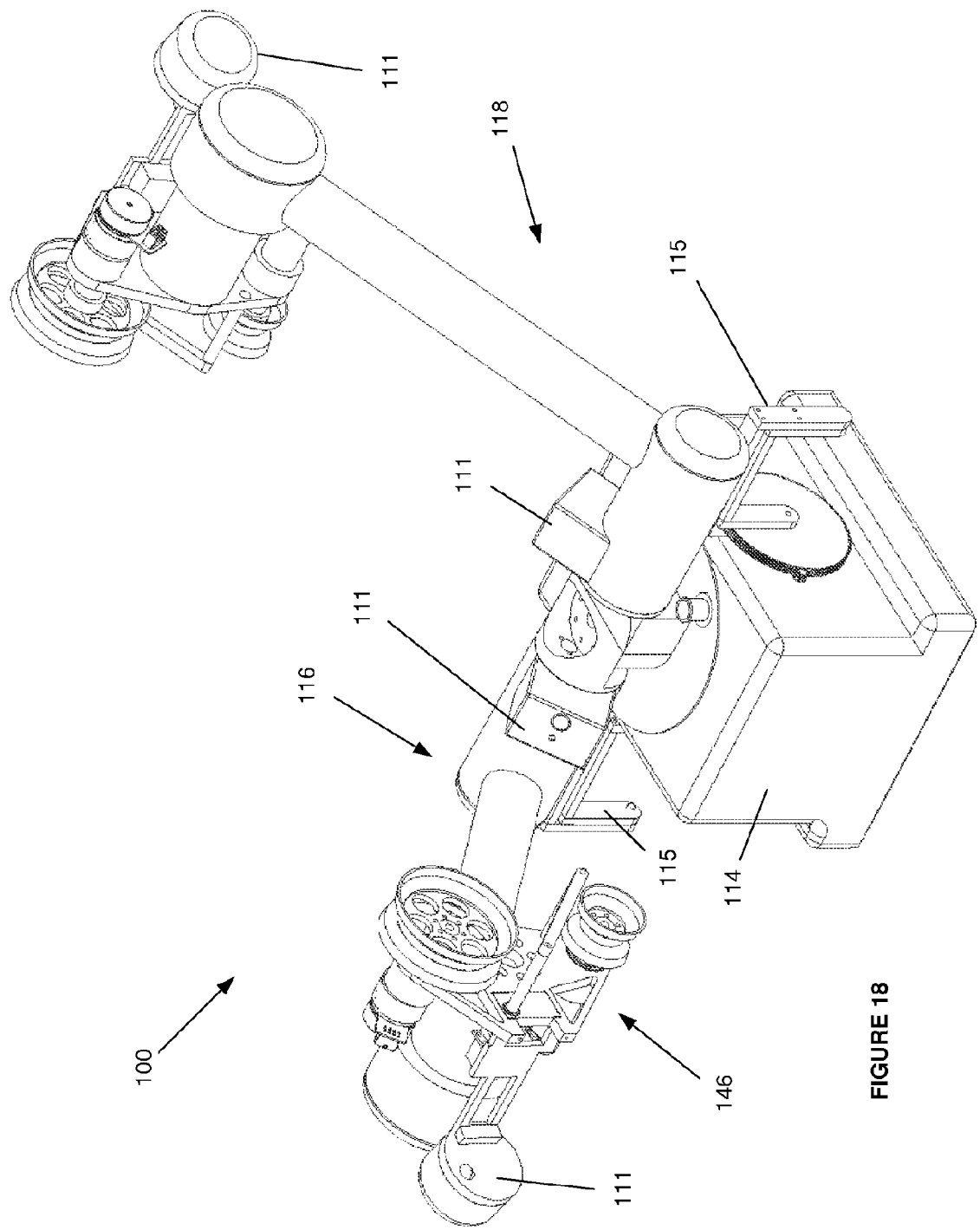
FIG. 18 shows a perspective view of another example embodiment of apparatus in accordance with the invention for use on a cable, particularly a power cable.
Figure 19:
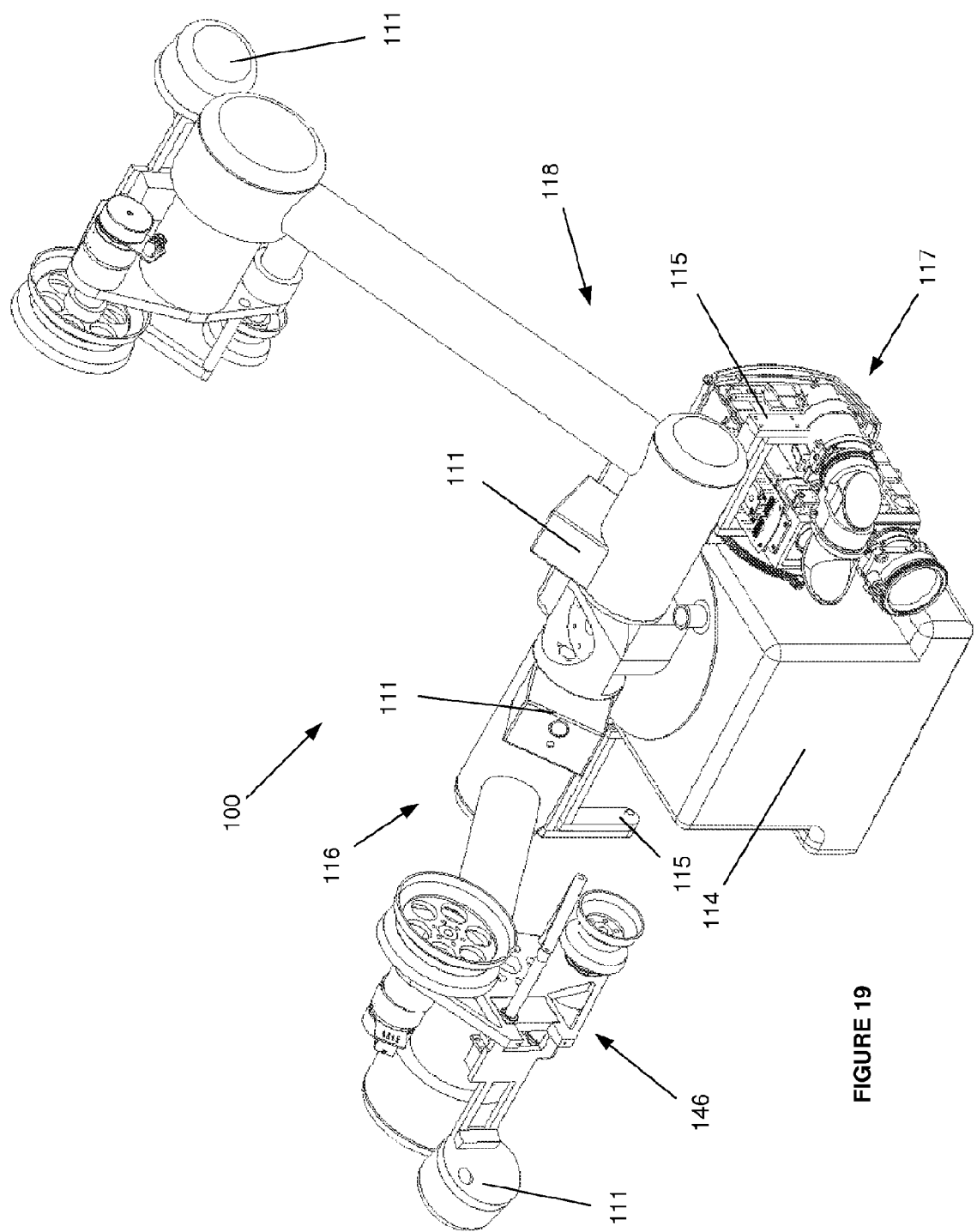
FIG. 19 shows a perspective view of yet another example embodiment of apparatus in accordance with the invention for use on a cable, particularly a power cable.

Referring now to FIGS. 18 and 19 of the drawings where another example embodiment of an apparatus in accordance with the invention is generally indicated by reference numeral 100. The apparatus 100 is substantially similar to the apparatus 10 as hereinbefore described and similar parts will not be discussed in great detail.

The apparatus 100 differs from the apparatus 10 in that it comprises additional situational awareness cameras 111 and a different transformer arrangement 116. In addition, camera bays 115 are provided flanking the payload body 114, which payload body 114 is differently shaped to the body 14. The apparatus 100 also includes a pan and tilt gimbal arrangement wherein the camera bays 115 are a smaller part of the whole gimbal. The gimbal arrangement includes a panning mechanism adjacent to the payload body 114. The payload body 114 which houses the payload is connected to the panning mechanism (so that it would not interfere with the gimbal movements) and the tilt mechanisms on either side of the box. That is, there are two camera bays 115 that are independently tiltable, but pan together. In FIG. 19, the apparatus 100 is illustrated with additional equipment operatively attached thereto, for example, an inspection camera.

In any event, it will be noted that each gripper arrangement 126 has a camera 111 attached to its rotating structure, and each link 116, 118 has a camera 111 attached to its rotating structure. The situational awareness cameras 111 are pointed at the line and provide all-round view of the line. They are fitted with wide field-of-view lenses such that they are able to provide both a close up, detailed view of the line/obstacle, as well as simultaneously providing a view substantially far ahead of the apparatus 100.

Figure 20:
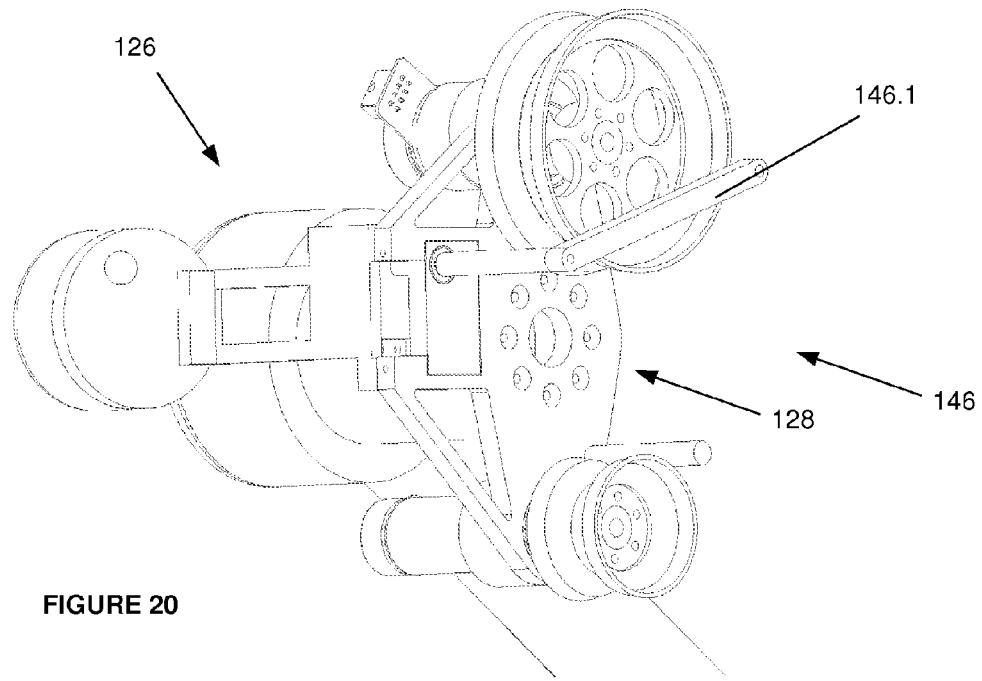
FIG. 20 shows a perspective view of a portion of the apparatus of FIGS. 18 and 19 with a transformer arrangement in a first open position.
Figure 21:
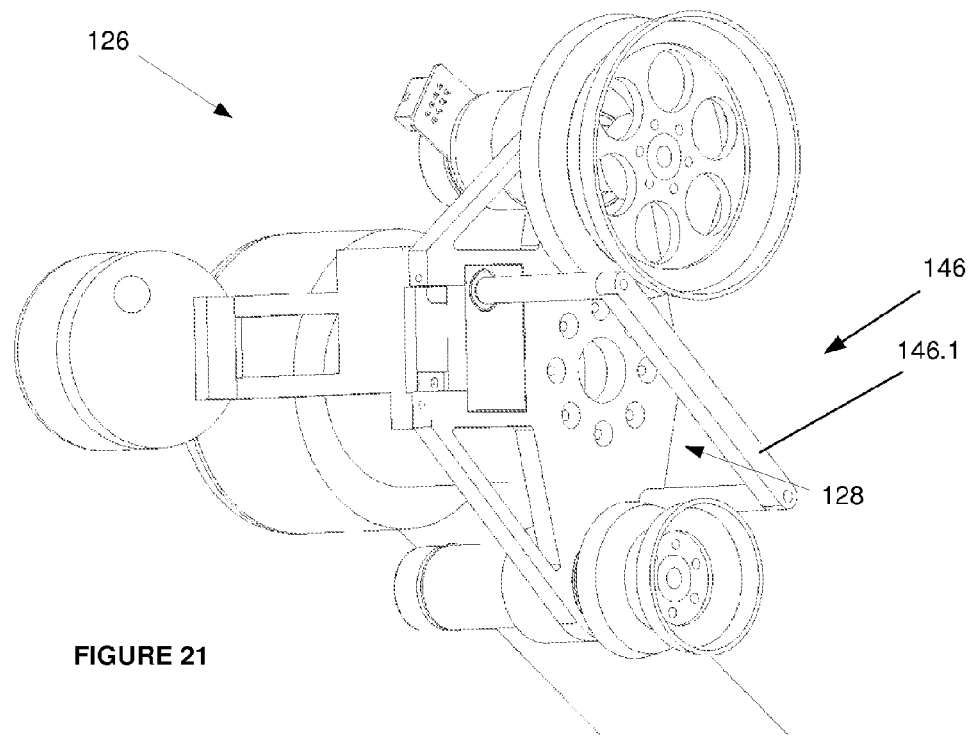
FIG. 21 shows a perspective view of a portion of the apparatus of FIGS. 18 and 19 with a transformer arrangement in a closed second position.

In addition, as best seen in FIGS. 20 and 21, each gripper arrangement 126 comprises a transformer arrangement 146 comprising a securing member 146.1 controllable to be rotatably displaceable between a first open position of the arrangement 146 in which the cable may be located in the zone 128 as illustrated in FIG. 20 and a second closed position of the arrangement 146 in which the cable is secured by the securing member 146.1 in the zone 128. In this way the apparatus 100 may not easily be displaced from attachment from the cable in the field, for example, under strong wind. The substantially closed loop formed by the member 146.1 which effectively surrounds the energised electrical cable may be used by the transformer arrangement 146 in a similar manner as described above to provide power for operating the apparatus, in use. However, the apparatus 100 may also or instead operate on conventional chemical fuel cells, solar power means, wind powered means, and the like.

Although not illustrated, it will be appreciated that instead of multiple joints as described above, the pair of links of the apparatus in accordance with the invention may be serially coupled via one controllable joint such that the links are displaceable relative to each other. In one example embodiment, the controllable joint may be a core joint or link joint or both core and link joints to provide the necessary degrees of freedom to manoeuvre the apparatus. Whatever, the configuration, it is important that the one gripper arrangement attached to the line acts as a base for the detached or gripper in the disengaged position arrangement or end effector to be manoeuvred in a serial manipulator fashion as hereinbefore described extensively.

The present invention exploits existing actuators to move the payload body 14 without the need for separate mechanisms to shift the centre of mass. This reduces weight and overall complexity of the invention.

The invention claimed is:

1. An apparatus for use on a cable, the apparatus comprising:
   a power module adapted to power the apparatus;
   at least one pair of links serially coupled via at least one joint such that the links are displaceable relative to each other;
   a gripper arrangement coupled to each link, the gripper arrangements being adapted for attaching the apparatus to the cable, wherein each gripper arrangement is controllable to grip and/or release the cable;
   a control arrangement comprising one or more processors configured at least to control displacement of the links and the gripper arrangements to grip and/or release the cable, in use; and
   one or more of inspection, monitoring, and maintenance systems.

2. An apparatus as claimed in claim 1, wherein the gripper arrangement is controllable to grip or release the cable as an end effector, or grip the cable as a base.

3. An apparatus as claimed in claim 1, wherein the gripper arrangement comprises at least two spaced apart gripper fingers, the gripper arrangement being controllable to displace one or both of the gripper fingers relative to the cable thereby to engage the cable.

4. An apparatus as claimed in claim 3, wherein the gripper arrangement is controllable to grip the cable in first and second engagement positions, and release the cable in a disengaged position, wherein in the first engagement position, both gripper fingers engage the cable, substantially on opposite sides of the cable; wherein in the second engagement position, only one gripper finger engages the cable; and wherein in the disengaged position, both gripper fingers disengage from the cable.

5. An apparatus as claimed in claim 4, wherein the gripper arrangement comprises a gripper frame connected in a serial fashion to the link via a gripper joint, wherein the two gripper fingers are provided on the gripper frame and are spaced apart by a cable locating zone such that, in use, actuation of the gripper joint while the cable is located in the cable locating zone causes the gripper fingers to grip or release the cable.

6. An apparatus as claimed in claim 5, wherein the gripper joint is either a revolute joint such that the gripper frame is substantially rotatable relative to the link on actuation of the revolute joint to grip or release the cable; or a prismatic joint such that the gripper frame, or part thereof, is substantially linearly displaceable relative to the link on actuation of the prismatic joint to grip or release the cable.

7. An apparatus as claimed in claim 1, wherein the at least one joint coupling the links is a revolute core joint operable to displace at least one link substantially about a first axis, or a revolute link joint operable to displace at least one link substantially about a second axis transverse to the first axis, in use.

8. An apparatus as claimed in claim 5, wherein, in use, the apparatus is a serial manipulator, or operates in a serial manipulator fashion, in that one gripper arrangement gripping the cable in the first engagement position serves as a base, and the other gripper arrangement in the disengaged position serves as an end effector.

9. An apparatus as claimed in claim 3, wherein one or both gripper fingers are wheels.

10. An apparatus as claimed in claim 9, wherein the apparatus comprises drive means drivingly coupled to one or both the wheels thereby to selectively cause rotation of one or both the wheels thereby to facilitate moving the apparatus longitudinally along the cable, in use.

11. An apparatus as claimed in claim 9, wherein one or both wheels comprise a circumferentially extending groove comprising traction means disposed therein to receive the cable therein, in use.

12. An apparatus as claimed in claim 3, wherein in the first engagement position, further actuation of the gripper joint provides another degree of freedom to the apparatus as the apparatus is caused to displace relative to the line.

13. An apparatus as claimed in claim 1, wherein each link comprises an elongate first portion extending transversely from a second portion having a longitudinal axis, wherein second portions of the links are coupled via the at least one joint.

14. An apparatus as claimed in claim 13, wherein second portions of the links are coupled to a revolute core joint, and wherein at least one second portion is coupled to the revolute core joint via a revolute link joint, wherein actuation of the revolute link joint causes rotational displacement of the link about the longitudinal axis of the second portion and actuation of the revolute core joint causes rotational displacement of one or both links about an axis perpendicular to the longitudinal axis of the second portion.

15. An apparatus as claimed in claim 14, wherein both second portions of the links are coupled to the core joint via link joints.

16. An apparatus as claimed in claim 1, wherein the cable is a power cable, wherein the power module comprises a transformer arrangement to draw power from the power cable, and wherein the transformer arrangement is operable to serve as a safety device to prevent the apparatus from falling from the power cable, in use.

17. An apparatus as claimed in claim 15, wherein each link comprises resistive portions or elements, thereby to facilitate a measurement determining module determining a voltage drop across the span of two links when both grip the power cable, thereby to facilitate determining at least electrical resistance of a splice.

18. An apparatus as claimed in claim 15, wherein the links comprise electrical fuse portions or elements to serve as fail-safe mechanisms should the apparatus fall out of an electrical clearance window of a power cable to which the same is attached.

19. An inspection and/or monitoring system for inspecting a cable, the inspection system comprising:
   a database for storing data; and
   a receiver module configured to receive one or more signals comprising data associated with the cable from at least one apparatus comprising a power module adapted to power the apparatus; at least one pair of links serially coupled via at least one joint such that the links are displaceable relative to each other; a gripper arrangement coupled to each link for attaching the apparatus to the cable, wherein each gripper arrangement is controllable to grip and/or release the cable; and a control arrangement comprising one or more processors configured to control displacement of the links and the gripper arrangements to grip and/or release the cable, in use.

20. A method of operating an apparatus on an elongate cable to avoid an obstacle, wherein the apparatus comprises a power module adapted to power the apparatus; at least one pair of links serially coupled via at least one joint such that the links are displaceable relative to each other; a gripper arrangement coupled to each link for attaching the apparatus to the cable, wherein each gripper arrangement is controllable to grip and/or release the cable; and a control arrangement comprising one or more processors configured to control displacement of the links and the gripper arrangements to grip and/or release the cable, in use, the method comprising:
   operating the gripping arrangement of one link of the apparatus to grip the cable such that the same serves as a base;
   operating the gripping arrangement of the other link of the apparatus to release the cable thereby freeing up the same for spatial displacement as an end effector; and
   causing displacement of the links relative to each other and/or the base relative to the associated link thereby to move the end effector to a region on the cable, or jumper cable, beyond the obstacle; and
   causing the end effector to engage and grip the cable, or jumper cable, beyond the obstacle.

* * * * *